(12) United States Patent
M.

(10) Patent No.: US 8,389,024 B2
(45) Date of Patent: Mar. 5, 2013

(54) ABSCISIC ACID AGAINST CANCER

(76) Inventor: Gonzalo Romero M., St. Petersburg, FL (US)

( * ) Notice: Subject to any disclaimer, the term of this patent is extended or adjusted under 35 U.S.C. 154(b) by 372 days.

(21) Appl. No.: 12/655,006

(22) Filed: Dec. 22, 2009

(65) Prior Publication Data
US 2010/0172977 A1 Jul. 8, 2010

Related U.S. Application Data

(63) Continuation-in-part of application No. 11/472,128, filed on Jun. 21, 2006.

(60) Provisional application No. 60/692,617, filed on Jun. 22, 2005.

(51) Int. Cl.
A61K 36/00 (2006.01)
(52) U.S. Cl. ........................................ 424/725; 514/557
(58) Field of Classification Search .................... 424/725
See application file for complete search history.

(56) References Cited

U.S. PATENT DOCUMENTS

| 3,958,025 A | 5/1976 | Livingston |
| 4,434,180 A | 2/1984 | Visscher |
| 2008/0242705 A1 | 10/2008 | Zocchi et al. |
| 2010/0216883 A1 | 8/2010 | Bassaganya-Riera et al. |

FOREIGN PATENT DOCUMENTS

| CN | 1686174 A | 10/2005 |
| CN | 1732808 A | 2/2006 |
| CN | 1748674 A | 3/2006 |
| EP | 0018406 A1 | 11/1980 |
| WO | WO2007092556 A2 | 8/2007 |
| WO | WO2008092297 A1 | 8/2008 |

OTHER PUBLICATIONS

Acevedo H. F. 2002. Human chorionic gonadotropin (hCG), the hormone of life and death: a review. J. Exper. Therapeutics and Oncology 2: 133-145.
Acevedo H.F et al. 1985. Expression of human choriogonadotropin-like material in coagulase-negative Staphylococcus species. Infection and Immunity 50(3): 860-868.
Addicott F.T et al. 1969. Physiology of abscisic acid and related substances. Ann. Reviews. Plant Physiol 20: 139-164.
Adey W.R. 1988. In: Biological coherence and response to external stimuli, H. Frohlich, ed., Heidelberg, Springer-Verlag, pp: 148-170.
Aidley D.J et al. 1996. Ion channels: molecules in action. Cambridge University Press. New York.
Allan A. C et al. 1994. Abscisic acid and gibberellin perception: inside or out? Plant Physiol 104: 1107-1108.
Ambrose E.J et al. 1956. Differences between the electrical charge carried by normal and homologous tumour cells. Nature 177: 576-577.
Anderson B. E et al. 1994. Evidence for an extracellular reception site for abscisic acid in Commelina guard cells. Plant Physiol 104: 1177-1183.

Assante G et al. 1977. (+)-Abscisic acid, a metabolite of the fungus Cercospora rosicola. Experientia 33: 1556-1557.
Astle M.C et al. 1980. A study of abscisic acid uptake by apical and proximal root segments of Phaseolus coccineus L. Planta 150: 312-320.
Becker R.O. 1974.The basic biological data transmission and control system influenced by electrical forces. Part II: Biological studies. Ann. N. Y. Acad. Sci 238: 236-241.
Behl et al. 1979. On the action of abscisic acid on transport, accumulation, and uptake of K + Z. Pflanzenphysiol. Bd. International Journal of Plant Physiology 95(1):335-353.
Beijersbergen A et al.1992. Conjugative transfer by the virulence system of Agrobacterium tumefaciens. Science 256: 1324-1327.
Bennett E et al. 1997. Contribution of sialic acid to the voltage dependance of sodium channel gating: a possible electrostatic mechanism. J. Gen. Physiol 109: 327-343.
Binggeli R et al. 1986. J. Theor. Biol 123: 377-401.
Blank M. 1987. The surface compartment model:a theory of ion transport focused on ionic processes in the electrical double layers at membr.Bioch et Biophy Acta 906: 277-294.
Blatt M.R. 1992. K+ channels of stomatal guard cells: characteristics of the inward rectifier and its control by pH. J. Gen. Physiol 99: 615-644.
Bornman C.H et al. 1967. Abscisin, auxin and gibberellin effects on the developmental aspects of abscission in cotton (Gossypium hirsutum). Amer. J. Bot 54(1): 125-135.
Bortner C.D et al. 1997. A primary role for K+ and Na+ efflux in the activation of apoptosis. J. Biol. Chem 272(51): 32436-32442.
Brewer A. K. 1984. The high pH therapy for cancer. Test on mice and humans. Pharmacol. Biochem & Behavior 21, suppl 1, pp. 1-5.
Brillouin L. 1966. Giant molecules and semiconductors. In: de Broglie L (ed) wave mechanics and molecular biology. Reading MA : Addison-Wesley.
Bruzzone S et al. 2007. Abscisic acid is an endogenous cytokine in human granulocytes with cyclic ADP-ribose as second messenger. PNAS 104-5759-5764.
Bruzzone S et al. 2008. The J Biol Chemistry 283(47): 32188-32197.
Casiday R et al. 1999. Washington University, St. Louis. Internet document www. chemistry.wustl.edu/~edudev/LabTutorials/Buffer/Buffer.html.
Catteral W.A et al. 1992. Molecular properties of the sodium channel: a receptor for multiple neurotoxins. Bulletin de la Societe de Pathologie Exotique 85 (5pt2): 481-485.
Cone C.D. Jr. 1974. The role of the surface electrical transmembrane potential in normal and malignant mitogenesis. Ann. N. Y. Acad. Sciences 238: 420-435.

(Continued)

Primary Examiner — Jake M. Vu

(57) ABSTRACT

ABSCISIC Acid (ABA) a naturally occurring plant hormone has been identified in this invention with potent properties to fight cancer. ABA is able to produce a hyperpolarization condition on plasma membrane through a decrease of intracellular Na+ and K+. Such phenomenon is produced in cancer cells by mediation of ion channel and activation of the signaling g-protein pathway. ABA aborting sustained depolarization in malignant tissue will produce a change in the configurational state of cell from a damage to a normal state. additionally, a positive polarization of hCG outer layer accomplished through a removal of electrons will permit immune system cells coming close to cancer cells for destruction.

12 Claims, 6 Drawing Sheets

OTHER PUBLICATIONS

Cohen H et al. 1976. Bacterial synthesis of substance similar to human chorionic gonadotropin. Proc. Soc. Exper. Biol. Medicine 152: 408-410.
Cope F.W.1978.A medical appl of the Ling association-induction hypothesis: the high potassium, low sodium diet of the Gerson cancer therapy.Physiol.Chem.Phys 10(5):465-468.
Coursol et al. 2003. Sphingolipid signalling in *Arabidopsis* guard cells involves heterotrimetric G proteins. Nature 423: 651-654.
Davies R.J et al. 1987. Sodium transport in a mouse model of colonic carcinogenesis. Cancer Research 47: 4646-4650.
Dekock P.C et al.1978. Effect of abscisic acid and benzyl adenine on the inorganic and organic composition of the Duckweed, *Lemna gibba* L. New Phytol 81: 505-511.
Delong R.P. et al. 1950. The significance of low calcium and high potassium content in neoplastic tissue. Cancer Journal American Cancer Society, 3: 718-721.
Devlin R. M. 1966. Plant physiology. Reinhold Pub Corp. New York.
Dietz K.J et al. 2000. Extracellular B-glucosidase activity in barley involved in the hydrolysis of ABA glucose conjugate in leaves. J. Exper. Botany 51(346): 937-944.
Donato L.J et al. 2005. Cancer Res 65(18): 8193-8199.
Ehrhorn Kruse M. 2006. The importance of abscisic acid as possible new drug in cancer treatment and its role on HCG. Thesis. South Denmark Univ. Dep of Biochem and Mol Bio.
Ehrlich P. 1909. Ueber den jetzigen Stand der Karzinomforschung. Ned. Tijdschr. Geneeskd 5(1): 273-290.
Fingrut O et al. 2002. Plant stress hormones suppress the proliferation and induce apoptosis in human cancer cells. Leukemia 16: 608-616.
Freemantle S.J et al. 2006. The retinoic acid paradox in cancer chemoprevention. J. Ntl.Cancer. Inst. Editorials 98 (7): 426-427.
Galston A.W. 1994. Life processes of plants. W.H. Freeman, NY.
Garnett M. 1998. First pulse: a personal journey in cancer research . New York, NY: First pulse projects.
Gerson M. 1978. The cure of advanced cancer by diet therapy: a summary of 30 years of clinical experimentation. Phisiol. Chem & Physics 10: 449-464.
Glinka Z et al. 1971. Abscisic acid raises the permeability of plant cells to water. Plant Physiol 48: 103-105.
Glinka Z et al. 1972. Induced changes in permeability of plant cell membranes to water. Plant Physiol 49: 602-606.
Goller D.A et al. 1986. Transmural electrical potential difference as an early marker in colon cancer. Arch Surg 121(3): 345-350.
Gomez-Angelats et al. 2000. Cell volume regulation in immune cell apoptosis. Cell Tissue Res 301(1): 33-42.
Haltiwanger S. 2003. The electrical properties of cancer cells. Internet document: www.royalrife.com/haltiwanger1.pdf.
Hartung W et al. 1980. Effect of abscisic acid on membrane potential and transport of glucose and glycine in *Lemna gibba* G1. Planta 148: 256-261.
Hartung W et al. 1991. New Phytol 119: 361-382.
Hartwell J.L. 1982. Plants used against cancer: a survey. Lawrence, MA. Quarterman Publications;pp: 438-439.
Hemberg T et al. 1961. The inhibitor β complex from resting potato tubers as an inhibitor of α- amylasa. Physiologia plantarum 14: 861-867.
Hess B et al. 2009. Cation specific binding with protein surface charges. PNAS 106(32): 13296-13300.
Ho M-W. 1998;1993. The Rainbow and the worm: the physics of organisms. 2nd ed. River Edge: World scientific.
Hodgkin A. L et al 1952. A quantitative description of membrane current and its application to conduction and excitation in nerve. J. Physiol 117: 500-544.
Hornberg C et al. 1984. High-affinity binding sites for abscisic acid on the plasmalemma of *Vicia faba* guard cells. Nature 310: 321-324.
Humble et al. 1971. Stomatal opening quantitatively related to potassium transport. Plant Physiol 48: 447-453.
Ilan N. et al. 1994. External pH effects on the depolarisation-activated K-channels in guard-cell. protoplasts of *Vicia faba*. J. Gen. Physiol 103: 807-831.
Kelen M et al. 2004. Turk J. Chem 28: 603-610.
Kennedy 5. K. 2003. Plants and people share a molecular signaling system, researchers discover. Internet report www.eurekalert.org/pub-releases/2003-06/ps-pap060503.php.
Khuri F.R et al. 2006.Randomized phase III trial of low-dose isotretinoin for prevention of second prim tumors in stage I, II head and neck cancer patients. JNCI:98:441-450.
Kondo et al. 1980. Effects of sulfite and pH on abscisic acid-dependent transpiration and stomatal opening. Plant Cell Physiol 21: 817-828.
Kondo et al. 1987. Plant Cell Physiol 28: 355-364.
Kramer E. M. 2006. How far can a molecule of weak acid travel in the apoplast or xylem?. Scientific Correspondence. Plant Physiol 141: 1233-1236.
Le Page-Degyvry M.T et al. 1986. Presence of abscisic acid, a phytohormone, in the mammalian brain. Proc. Natl. Acad. Sci 83: 1155-1158.
Lee K.H et al. 2006. Activation of glucosidase via stress-induced polymerization rapidly increases active pools of abscisic acid. Cell 126: 1109-1120.
Ling G.N. 1962. A physical theory of the living state: the association-induction hypothesis. Blaisdell, Waltham, Mass.
Livingston V. W-C. 1984. The conquest of cancer: vaccines and diet. Franklin Watts, New York, NY.
MacRobbie E.A.C. 1997. Signalling in guard cells and regulation of ion channel activity. Journal -Exper. Botany 48: 515-528.
Mahnensmith et al. 1985. Circulation Research. An Official Journal American Heart Association. 56(6): 773-788.
Mann C.L et al. 2001. Glucocorticoid-Ind plasma mem depol during thymocyte apop: association with cell shrinkage and deg of Na-K ATPase. Endocrinology 142(12): 5059-5068.
Mansfield T.A et al. 1971. Effects of abscisic acid on potassium uptake and starch content of stomatal guard cells. Planta 101: 147-158.
Marban E et al. 1998. Topical review: structure and function of voltage-gated sodium channels. J. Physiol 508(3): 647-657.
Marino A.A et al. 1994. Association between cell membrane potential and breast cancer. Tumor Biol 15: 82-89.
Merck Index: an encyclopedia of chemicals, drugs and biologicals. 1996. Twelfth edition. Merck & Co, Inc. Whitehouse Station, NJ.
Milborrow B.V. 1974. The chemistry and physiology of abscisic acid. Ann. Rev. Plant Physiol 25: 259-307.
Milborrow B.V. 1967. The identification of (+)-abscisin II [(+)-dormin] in plants and measurement of its concentrations. Planta 76(2): 93-113.
Milborrow B.V. 1966. The effects of synthetic dl-dormin (abscisin II) on the growth of the oat mesocotyl. Planta 70: 155-171.
Nukui M et al. 2006. Normotonic cell shrinkage induced by Na+ deprivation results in apoptotic cell death in human epithelial HeLa cells. J. Phisiol. Sciences 56(5): 335-339.
Ogunkanmi A.B et al. 1973. An improved bio-assay for abscisic acid and other anti-transpirants. New Phytol 72: 277-282.
Oschman J.L. 2000. Energy medicine: the scientific basis. Edinburgh, England: Churchill Livingstone.
Outlaw W.H Jr. 1983. Currents concepts on the role of potassium in stomatal movements. Minireview. Physiol. Plantarum 59: 302-311.
Page C.C and Dutton et al 1999. How biol mol move electrons: simplicity trumps complexity. Inter doc www.sciencedaiily.com/releases/1999/11/991108085452.htm.Penn Med Ct Univ.
Paterson N.W et al. 1988. The effect of pH on stomatal sensitivity to abscisic acid. Plant Cell Environ 11: 83-89.
Pedron J et al. 1998. Eur. J. Biochem 252(3): 386-390.
Popova L.P et al. 2000. Abscisic acid-an intraleaf water-stress signal. Physiologia Plantarum 108: 376-381.
Puce S et al. 2004. Abscisic acid signaling through cyclic ADP-ribose in hydroid regeneration. J. Biol Chem 279 (38): 39783-39788.
Raikow R.B et al. 1987. Effects of human choriogonadotropin on malignant growth. Proc. Amer. Assoc. Cancer Res. 78th Ann Meeting 28: abstract 227 p. 57.
Sawhney B.L et al. 1969. Direct determination of potassium ion accumulation in guard cells in relation to stomatal opening in light. Plant Physiol 44: 1350-1354.

Scarfi S et al. 2008. Cyclic ADP-ribose-mediated expansion and stimulation of human mesenchymal stem cell by the plant hormone abscisic acid. Stem Cells 26: 2855-2864.

Schroeder J. I et al. 2006. A quick release mechanism for abscisic acid. Leading edge previews. Cell 126: 1023-1025.

Schroeder J. I et al. 2001. Guard cell abscisic acid signalling and engineering drought hardiness in plants. Nature 410: 327-330.

Singh B.N. et al. 1979. Abscisic acid levels and metabolism in the leaf epidermal tissue of *Tulipa gesnenana* L. and *Commelina communis* L. Planta 146: 135-138.

Stern R.G et al. 1999. Carcinogenesis and the plasma membrane. Medical Hypothesis 52(5):367-372.

Stuhmer W et al. 1989: Structural parts involved in activation and inactivation of the sodium channel. Nature 339: 597-603.

Szent-Gyorgyi A. 1978. The living state and cancer. New York: Marcel Dekker.

Tanada T. 1972. Antagonism between indolacetic acid and abscisic acid on a rapid phytochrome-mediated process. Nature 236: 460-461.

Tezcan F.A et al. 2001. Electron tunneling in protein crystals. PNAS 98(9): 5002-5006.

Tiralongo E. 2002. Trans-sialidase from *Trypanosoma congolense*: isolation, characterisation and molecular biology. Thesis dissertation. Bremen University. Germany.

Tsong T. Y. 1989. Deciphering the language of cells. Features. Talking points. Elsevier Science Publishers Ltd, (UK).

Tucker D.J. 1977. The effects of far-red light on later bud outgrowth in decap tomato plants and the assoc changes in the levels of auxin and ABA. Plant Sc Lett 8:339-344.

Tuteja N. 2007. Abscisic acid and abiotic stress signaling. Plant Signaling & Behavior 2(3): 135-138.

Ullrich C.I et al. 2000. Review article: vascularization is a general requirement for growth of plant and animal tumours. J. Exp. Botany 51 (353): 1951-1960.

Van Rinsum J et al. 1986. Specific inhibition of human natural killer cell-mediated cytotoxicity by sialic acid and sialo-oligosaccharides. Int. J. Cancer 38: 915-922.

Van Slyke D.D. 1933. Chapter certain aspects of the physical chemistry of the blood. In Physical chemistry of blood pp: 184-189. New York.

Vanyushin B.F et al. 2004. Apoptosis in plants: specific features of plant apoptotic cells and effect of various factors and agents. Int Rev Cytol 233:135-179.

Verhaert P et al. 1986. Subst resembling peptides of the verteb gonadotropin system occur in the central nervous system of *Periplaneta americana*. Insect Biochem 16: 191-197.

Walton D.C. 1980. Biochemistry and physiology of abscisic acid. Ann. Rev. Plant Physiol 31: 453-489.

Warburg O. 1925. The metabolism of carcinoma cells. J. Cancer Research 9: 148-163.

Wilkinson S et al. 1997. Plant Physiol 113: 559-573.

Wilmer C.M et al. 1969. Active cation transport and stomatal opening: a possible physiological role of sodium ions. Z.Flanzenphysiol. Bd 61(S): 398-400.

Windsor M.L et al.1992. The uptake of (+)-S- and (−)-R-abscisic acid by suspension culture cells of Hopbush (*Dodonaea viscosa*). Plant Physiol 100:54-62.

Zeevaart J.A.D et al. 1988. Metabolism and physiology of abscisic acid. Ann. Rev. Plant Physiol. Plant Mol. Bio. 39: 439-473.

Zhang X et al. 2001. K+ channels inhibited by hydrogen peroxide mediate abscisic acid signaling in *Vicia* guard cells. Cell Research 11(3): 195-202.

Zhao H.W et al. 2007. Effect on induction of differentiation of TCA8113 cells affected by abscisic acid in vitro. Hua Xi Kou Qiang Yi Xue Za Zhi. October 25(5):508-512.

Zocchi E et al. 2001. The temper-signaling cascade in sponges involves a heat-gated cation channel, ABA, and cyclic ADP-ribose. Proc. Natl. Acad. Sci. USA 98(26):14859-14864.

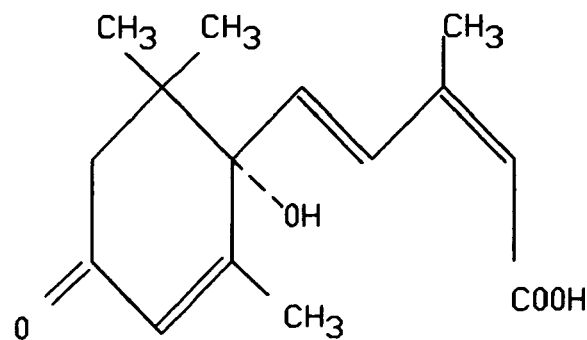
← FIG. 1
FIG. 2 →
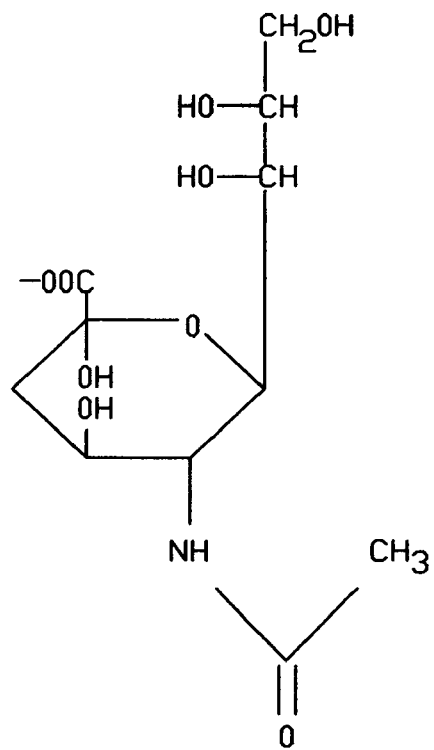

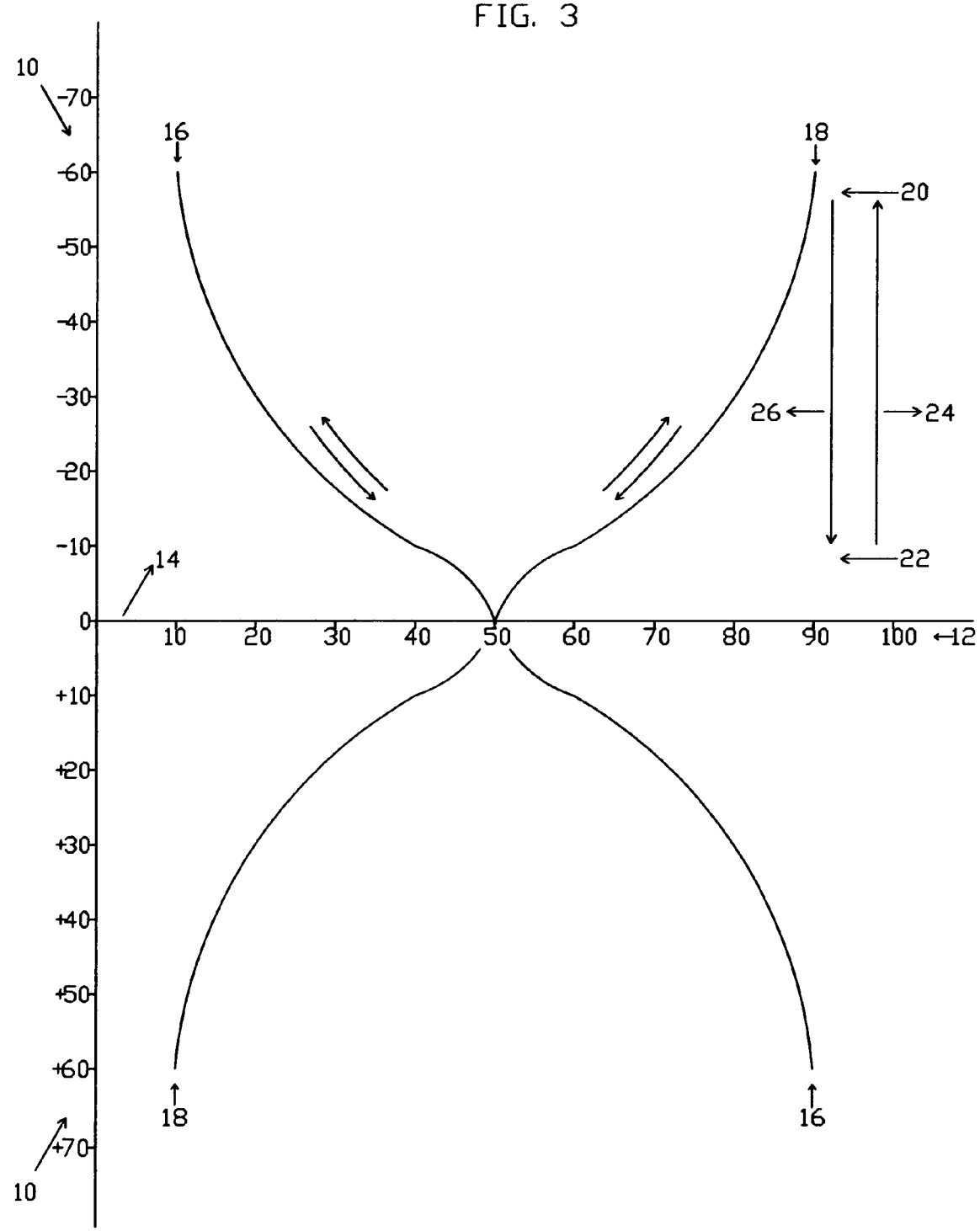

ABSCISIC ACID AGAINST CANCER

CROSS-REFERENCE TO RELATED APPLICATIONS

This application is a continuation in part of patent application Ser. No. 11/472,128 filed on Jun. 21, 2006, which is based upon and entitled to the benefit of the provisional patent application Ser. No. 60/692,617 filed Jun. 22, 2005, the subject matter of which applications is incorporated herein by reference.

FIELD OF THE INVENTION

This invention has been found in the field of medical treatments of drugs biologically affecting the human body and related to counteracting different types of cancer, which have potentially unlimited growth and expand locally by invasion and systemically by metastasis.

BACKGROUND OF THE INVENTION

Description of the Prior Arts

Abscisic acid (ABA) is a natural occurring plant hormone also denominated Abscisin II or Dormin. It is chemically named as [S-(Z,E)]-5-(1-Hydroxy-2,6,6-trimethyl-4-oxo-2-cyclohexen-1-yl)-3-methyl-2,4-pentadienoic acid (Merck Index 1996, p. 2). ABA molecular structure is showed in FIG. 1.

ABA structure is a 15-c sesquiterpene synthesized in chloroplasts and likely also under extrachloroplasts biosynthetic pathway. ABA is a weak acid ($C_{15}H_{20}O_4$) soluble in many organic solvents. Addicott et al. 1969, Milborrow 1974, and Walton 1980 have studied its physical and chemical properties.

The natural compound has been indicated as (S) or (+), its synthetic or racemic substance as (RS) or (+/−), and its enantiomer as (−).

ABA natural form (+), synthetics or enantiomers, related and derivatives, all of these are subjects of the present invention.

Some of the ABA related and derivatives mentioned here are: 2-trans-abscisic acid; phaseic acid; 2-trans-phaseic acid; (+)-abscisyl-beta-D-glucopyranoside; (R)-abscisic acid; 2,4-trans, cis-abscisic acid. Addicot et al. 1969, p. 144, has all those substances pictured. In addition, Milborrow 1974, pp. 261-272, has defined the following chemical structures: 1',4'-cis-diol of (+)-abscisic acid; 1',4'-trans-diol of (+)-abscisic acid; (+)-xantoxin (2-cis); (+)-xanthoxin (2-trans); (+)-xanthoxin acid (2-cis); xanthoxin acid methyl ester (2-cis-isomer); (+/−) abscisic alcohol; (+/−)-abscisic aldehyde. Also Milborrow 1974 has characterized the following forms: XIII, XIV, XV, XVI, XVII, XVIII, XIX, XX, XXI, XXII, XXIII, XXIV, XXV, XXVI, XXVII, XXVIII, XXIX, XXX, XXXI, XXXII, XXXIII, XXXIV, XXXV, XXXVI, XXXVII, XXXVIII, XXXIX, XL, XLI, XLII, XLIII, XLIV, XLV, XLVI, XLVII, XLVIII, XLIV, XLV, XLVI, XLVII, XLVIII, XLIX, L, LI, LII, LIII, LIV, LV, LVI, LVII, LVIII, LIX, LX, LXI, LXII, LXIII, LXIV, LXV. Many of those mentioned substances have been found by researchers generating a variety of effects in plants.

ABA as a potent inhibitor has been studied through an extensive bibliographical reference in biochemical and physiological mechanisms such as: water stress and stomatal control, dormancy, abscission, senescence, growth inhibition, and hydraulic conductivity.

In relation to seed dormancy, exogenous ABA prevented precocious germination of immature embryos of several species when cultured in vitro, and, ABA produced this phenomenon during the early stages of embryogenesis (Zeevaart Jan A. D et al. 1988). Abscission which is a lysigenous breakdown of cells accelerated by a rapid development of pectinases, cellulases, and proteases has been suggested by Borman et al. 1967, p. 125, and by Addicot et al. 1969, p. 156. Senescence, identified by multiple effects such as fruit maturation, aging and plant death has been observed by Milborrow 1974, p. 293. In addition, Glinka et al. 1971, 1972 and Windsor et al. 1992, p. 59, have mentioned an increase of membrane permeability caused by ABA. Ethylene has been related to the phenomenon of abscission and fruit maturation.

Plant Growth Inhibition

ABA inhibited oat mesocotyl growth by increasing ABA or dormin concentrations, whatever levels of indol acetic acid (IAA) or gibberellins (GA) were given (Milborrow, 1966, p. 154). ABA also inhibits tomatoes lateral buds outgrowth (Tucker, 1977). Probable changes in tissue growth by ABA effects might be provoked in nucleic acids and protein metabolism (Dekock et al. 1978, p. 508). According to Zeevaart Jan A. D. et al. 1988, page 457, ABA can inhibit root growth as well as promote growth of this organ. ABA root growth contradictory effects are explained, because enlarge of the root system is combined with increased hydraulic conductance and water uptake. The latter effects are considered mechanisms to defend the plant against water stress.

Stomatal Movements

ABA acts in many physiological processes in plants, especially during stomatal closure in conditions of limited water supply. Stomatal closure involves loss of ions and reduction of osmotic pressure (Mansfield et al. 1971, p. 147; Dekock et al. 1978, p. 506; Macrobbie, 1997, p. 515). ABA loss or entry of anions and cations is mediated by signalling activation of ion channel (Schroeder et al. 2001, p. 328; Macrobbie, 1997, p. 515).

As it expresses the former statement, stomatal movements are correlated to increase or decrease of guard cells osmotic contents. These osmotic changes, cause water to move in or out from guard cells, causing them to either expand (become turgid) or become dehydrated. The stomate is open when it expands and is closed when it becomes dehydrated. Different thick of the guard cell wall causes stomates to open. The wall, which is adjacent to the pore is thicker and less elastic and flexible than the external wall. Turgor will produce, the external wall to expand more than the internal wall, which is close to the pore.

Apparently ABA in the apoplast must be inhibited or moved during plant rewatering, which starts to open stomata. Inhibition mechanisms probably comprise: relocation of the hormone in other plant compartments outside the stomatal complex, ABA uptake into cytoplasm to be metabolized or stored, and inhibition of synthesis.

In normal conditions, stomatal opening and closure respond to light, without exogenous application of ABA. X-ray images in tobacco leaves demonstrate a $K^+$ increase in guard cells as stomata open in the light, and a decrease as stomata close in the dark (Sawhney et al. 1969, pp. 1351-1353; Humble et al. 1971, pp. 448-450).

Definitively, ABA is involved in stomatal changes during the days and nights. According to Zeevaart Jan A. D. et al. 1988, page 456, the amount of ABA in the apoplast can double upon transfer to darkness or in response to a pH change in the chloroplast stroma during stress. A classical model proposes that, drought stress roots produce ABA, which is transported to the leaves via the xylem. Water stress may happen in roots by soil water deficiency and as well as in leaves caused by humidity conditions. According to Schroeder et al. 2006, page 1024, stress may occur in leaves by lowering the ambient humidity. It produces ABA release in leaves via hydrolysis of a pre-existing pool of inactive glucose-conjugated ABA (ABA-GE). This inactive form is located in vacuoles, xylem sap, and probably in the cytosol and cell wall as well (Dietz et al. 2000). Lee et al. 2006 demonstrate that, the cleavage of ABA-GE by an specific beta-glucosidase (ATBG1), is a mechanism for ABA release quick response to dehydration and also "day/night" conditions.

During normal stomatal opening, uptake of $K^+$ is mediated by $K^+$ ion pump (Sawhney et al. 1969, p. 1350). Outlaw 1983, in his review "Current Concepts on the Role of Potassium in Stomatal Movements", remarks in the abstract, p. 302, that $K^+$ uptake by plant cells is mediated by an ATPase that pumps protons across the plasmalema. In normal cells, cytoplasmic $K^+$ has a bigger concentration than $K^+$ in the apoplast, thus it seems obvious a use of energy by cells for transporting ions as $K^+$ against a concentration gradient. Loss and entry of ions are mechanisms involved in stomatal movements. Due to that, plasma membrane ion transport is closely correlated to cancer cell normalization and apoptosis, it is studied below in detail.

Loss of Solutes by ABA Effect

Mansfield et al. 1971, p. 147, showed in histochemical tests, that guard cell $K^+$ concentration of *C. communis* was reduced by ABA treatment, while the starch content of chloroplasts increased.

ABA also moves other cations as $Ca^{2+}$ to be transported inward. (MacRobbie 1997, p. 515; Schroeder 2001, p. 328), and anions to be transported outward (Schroeder 2001, p. 328).

Dekock et al. 1978, p. 506, working with *Lemna gibba* fronds and ABA, detected a marked intracellular decrease in $K^+$ and $Na^+$, an increase in Ca, Mg, Fe, and insoluble P and a marked decrease in P/Fe and K/Ca ratios.

MacRobbie 1997, page 515, also confirms and gives a better explanation of the phenomenon. ABA closes stomatal pores by inducing net loss of $K^+$ salts (including rubidium) from guard cells, involving net efflux of both anions and cations from the vacuole to the cytoplasm, as well as from the cytoplasm to the outside. ABA plasma membrane ion transport is produced by the activation of the ion channel and ion pump.

Humble et al. 1971, p. 451, under research of stomatal movements determined that $K^+$ is the specific ion involved, not showing significant importance, the rest of the ions. It takes relevance, due to that ABA also moves other cations as $Ca^{2+}$, to be transported inward and anions to be transported outward.

ABA also inhibits $K^+$ uptake, which is required to prevent stomatal opening (Schroeder et al. 2001, p. 328). According to Raschke K 1987 and Shimazaki K et al. 1986, ABA prevents stomatal opening by rapidly blocking $H^+$ extrusion and $K^+$ influx (cited in Zeevart Jan A. D et al. 1988). ABA in roots has a similar effect as it is exerted in leaves when it prevents stomatal opening. In excised barley roots of *Hordeum distichon*, ABA inhibits accumulation, transport and uptake of $K^+$ and $Na^+$ to avoid osmotic stress during drought (Behl et al. 1979, p. 335, vol 95, Number 1, International Journal of Plant Physiology). Here, it is also possible to observe $Na^+$ participation in stomatal control and definitive influence of ABA over cation $Na^+$. Wilmer et al. 1969, also demonstrated that $Na^+$ and $K^+$ are important in stomatal mechanisms.

According to research of Behl et al. 1979, already mentioned, it was found that ABA in barley roots inhibited the transport of both ions to a similar degree. It means that, ABA has no selectivity over $K^+$ and $Na^+$ under general conditions. Nevertheless, ABA may turn out to affect the uptake of $K^+$ and $Na^+$ differentially by stimulating the uptake of $Na^+$ only.

ABA Target Cells

A long time ago it has been discovered that, bits of tissue from almost any part of the plant could be excised and grown in cultures. The new cells are not usually organized as differentiated cells, but they produce a formless mass called callus. It can divide perpetually without any decrease of the growth rate if it is provided fresh medium time to time. On the plant, such cells may have a finite life span and form differentiated cells such as roots and buds, if the appropriate growth hormones are supplied (Galston A. W, 1994). ABA as plant hormone is directly involved in plant cell differentiation.

In plants, the ABA target cells are embryonic cells and meristems and differentiated cells as stomas. It has been proved ABA action in inhibition of seed and bud germination, and in control of stomatal closure.

It has also been defined that tumors are composed of highly aggressive undifferentiated cells and differentiated as well. Undifferentiated cells are biochemically similar to embryonic cells, because the increased expression of embryonic genes in such cells.

Stomas as cancer cells as well accumulate solutes and water. In plants, during the stage of stomatal opening, stomas store mainly $K^+$ and water. On the other hand, animal cancer cell accumulates $Na^+$ and water. An apoptotic process makes that, cells suffer a phenomenon of shrinkage, which is a mechanism physiologically similar to the mechanism of ABA stomata closure in plants.

Positive Polarization and Hyperpolarization Effect in Plasma Membrane

Tanada 1971, p. 461, in his study "Anatagonism Between Indoleacetic Acid and Abscisic Acid on a Rapid Phytochrome-Mediated Process", concluded that phytochrome acts in conjunction with hormones such as IAA and/or ABA to bring fast changes in surface charges. Tanada suggested, these hormones have opposing effects on the surface potentials: ABA inducing a positive and IAA inducing a negative potential. ABA plant synthesis location has been recognized in chloroplasts mediated by phytochrome's absorbing light, which increases ABA concentration. Tanada's experiment demonstrated that, red photons could increase concentration of ABA relative to that of IAA thereby bringing about a positive membrane potential, which causes adhesion of root tips to a negatively-charged glass surface.

Hartung et al. 1980, pp. 257-258, recorded a hyperpolarization effect of ABA in *Lemna gibba* G1 on a membrane electrochemical potential difference (EPD). Treatment with 10-100 mcm, ABA produced a potential increase in average of 85 mV. This research mentions that, a decreased intracellular $K^+$ concentration could generate membrane hyperpolarization of *lemna* cells. After 15 hours ABA treatment, EPD increased from −109 mV to −194 mV. $K^+$ outside of the cytoplasm causes a positive charge on plasma membrane and it increases charge difference between the cytoplasm and surface membrane.

EPD results, from a separation of positive and negative charges across the cell membrane. This separation of predominantly positive charges outside and negative charges inside the membrane at rest is maintained because the lipid bilayer acts as a barrier to the diffusion of ions. It gives rise to an EPD. The resting potential can be disturbed whenever there is a net ion efflux into or out of the cell. A reduction of the charge separation is called depolarization and an increase in charge separation is called hyperpolarization. In normal cells, a higher concentration of anions relative to $K^+$ mainly produces a net negative charge inside of cells. Net positive charges outside of cells is produced by a bigger concentration of $NA^+$ relative to CF. The main negative charge inside of cell is held by proteins, usually named intracellular protein matrix.

The ABA hyperpolarization phenomenon mentioned by Hartung et al. 1980 is distinct to the ABA positive polarization effect researched by Tanada 1971. The latter effect is a subtle phenomenon related intimately to the first one, which it will be disclose widely ahead in this invention.

ABA in Relation to a Physiological Relationship with Mammalians

Le page-Degivry et al. 1986, pp. 1155-1156, reported an ABA presence in the central nervous system of pigs and rats. ABA identification by using a radioimmunoassay in different tissues demonstrated a bigger amount of ABA found in brains than any of the other tissues. The final product of purification had the same properties as ABA, inhibiting stomatal aperture of abaxial epidermis strips of *setcreasea purpurea* boom (commelinaceae). They remarked that, the ABA presence can not be considered an ABA containing diet consequence, and suggested metabolic pathways identification for ABA biosynthesis in the brain.

ABA presence has been also reported in lower metazoa (marine sponges and hydroids) responding to environmental stimuli as temperature rise in sponges and light exposure in hydroids (Zocchi et al. 2001, Puce et al. 2004). In humans, ABA has been found stimulating several functions in immune system cells such as granulocytes, lymphocytes, fibroblasts, mesenchymal stem cells, platelets and monocytes (Bruzzone et al. 2007, Zocchi et al. 2008). Also ABA has been identified as an endogenous stimulator of insulin release in human pancreatic islets (Bruzzone et al. 2008).

Plant Hormone Effects in Humans

Naturally occurring cytokinins such as kinetin and zeatin, which intervene in plant cellular division have been promoted and patented in Europe and USA for treatment of human skin aging by an international biopharmaceutical corporation denominated Senetek. These patents have showed and proven that, kinetin is capable of delaying or preventing a host of age-related changes of human skin fibroblasts grown in laboratory culture.

Fibroblasts are believed to be at the center of age-related changes of the skin. These cells produce collagen and elastin, the two proteins most clearly tied to the development of wrinkles, sagging and laxity of the skin. Additionally, GA has been structurally found as molecules roughly analogous to the steroid group of animal hormones. Steroids have an enhancing effect in human cells and it has been used in sport activities for increasing musculature size. In plants, GA produces cellular elongation, which is a similar enhancing effect induced by steroids in humans.

ABA in Relation to the Disease of Cancer

This invention was initially started by considering that, plant hormones such as IAA, GA and cytokinins stimulate cellular growth in plants. Conversely, ABA manifests an antagonist effect in plants by producing cellular growth inhibition.

ABA was mentioned for the first time in relation to cancer by Dr. Virginia Livingston in her U.S. Pat. No. 3,958,025 (1976) denominated, "Abscisic Acid Tablets and Process". In this invention, she experimented with ABA in mice proving ABA neutralizing properties of a Microbic Chorionic Gonadotropin, which was similar to the Human Chorionic Gonadotropin (hCG).

Such statement defined by Dr. Livingston was essentially a complementary or collateral research, beside her central focus of investigation, which was about a type of tumor-associated bacteria named Progenitor cryptocides. According to Dr. Livingston, such bacterium expresses hCG, which turns it out in developing cancer. Such findings reported back in the early 1970's were erroneously dismissed. After Dr. Livingston's research, it was recognized that others types of tumor-associated bacteria also produce this hormone and cancer.

Some coagulase-negative *sataphylococcus* species isolated from cancer patients expressed hCG, but not every isolated bacterial strain did it, Acevedo (2002), p. 860. Such studies confirmed that, Progenitor cryptocides is not the unique bacterium expressing hCG as postulated by Livingston and Associates, but her conclusions and investigations were generally right. Dr. Livingston's findings were a first indication of a possible synthesis of a mammalian protein hormone by a microbial organism, Cohen et al. (1976), p. 410.

Likewise as it occurred with the central focus of Dr. Livingston's investigation, it also took place with her complementary, collateral and most important research as well, the ABA capacity of neutralizing hCG. The central topic of Dr. Livingston's research was in certain form verified aftermath, but not her complementary or collateral research, which it is motive and impulse of this invention.

In 1984 Dr. Livingston published her book "The Conquest of Cancer", in which she mentioned results on pp. 15-38, of applying in humans an integral treatment stimulating the immune system and administering ABA by a dietetic via.

Since Dr. Livingston's works, which were crystallized in researches, books and inventions, nobody else had studied and mentioned ABA in relation to cancer until 2005 and following years. During the year 2006, the invention number (CN 1748674A) published by The Chengdu Biological Institute Academy of Sciences, titled "New Use of Natural Abscisic Acid (ABA) in Developing Differentiation Inducer Drugs of Tumor Cells", experimentally determined that ABA is able to: make proliferating tumor cells stagnate in S-phase and stop cell division, become cancer cells in normal cells, produce apoptosis and inhibit angiogenesis in a variety of tumor cells. In addition, on 2006 and re-examining the Livingston-Wheeler contentions, Marianne Ehrhorn Kruse then in the Department of Biochemistry and Molecular Biology of the University of Southern Denmark, elaborated a master thesis titled "The Importance of Abscisic Acid as Possible New Drug in Cancer Treatment and its Role on Human Chorionic Gonadotropin Pathways". She found, that aba caused a tumor growth reduction, reduced cell proliferation rate, changed cell cycle progression, and produced induction of apoptosis, in four human cancer cell lines (HELA, DU145, HCT116 AND K562).

ABA identification as an endogenous cytokine in human granulocytes and demonstration of ABA presence in human lymphocytes, fibroblasts, mesenchymal stem cells, platelets and monocytes has significant importance in its role for fighting cancer cells.

ABA as plant hormone could have been transferred to animals during the evolution, it could confirm: ABA serious implications in animal and human metabolism and its identification as a new mammalian hormone. Previous knowledge of ABA plant induced effect has importance to explore such implications. Mostly, ABA has been studied around the world in connection to agricultural concerns, specifically about drought and water stresses.

OBJECTIVES OF THE INVENTION

1. Stimulate and encourage researchers to keep investigations going about ABA and its properties against cancer.

2. Define probable mechanisms of ABA to fight cancer.

3. Produce technical information that can be useful to make a clinical research and for manufacturing an adequate pharmaceutical medicine.

4. Verify and precise testimony expressed by Dr. Livingston about ABA capacity to neutralize the hormone of cancer.

DRAWINGS

The invention will be better understood and objectives other than those set forth above will become apparent when consideration is given to the following detailed description thereof. Such description makes reference to the annexed drawings wherein:

FIG. 1 is an illustration of the molecular structure of ABA.

FIG. 2 is an illustration of the molecular structure of Sialic acids (SIA).

FIG. 3 is an illustration of the curve of mechanism of $Na^+$ in proliferating normal cells.

Figure 4:
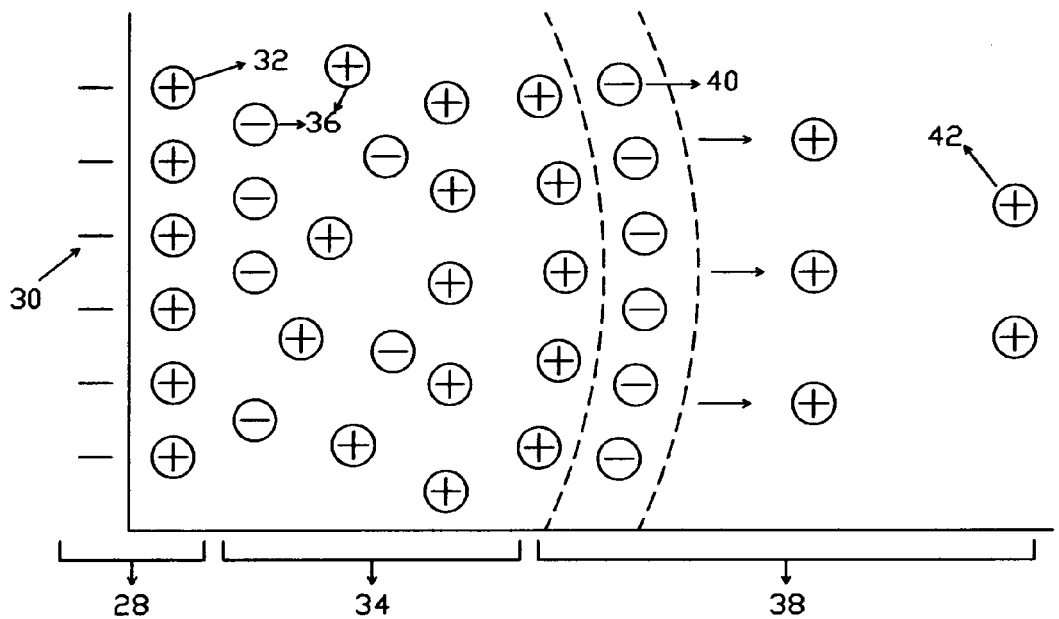
FIG. 4 is an illustration of the concentration gradient of $Na^+$ toward the extracellular fluid.

| REFERENCE NUMBERS | |
|---|---|
| 10 | Electrochemical potential difference (EPD) with values between 0 and −70 mv. |
| 12 | Sodium concentrations in percent. |
| 14 | Isoelectric point. |
| 16 | Curve of intracellular sodium concentration $[Na^+]$ i. |
| 18 | Curve of extracellular sodium concentration $[Na^+]$ e. |
| 20 | Quiescent stage. |
| 22 | Mitogenesis. |
| 24 | Hyperpolarization. |
| 26 | Depolarization. |
| 28 | First layer (stern layer). |
| 30 | Cancer cells plasma membrane showing negative charges. |
| 32 | Cations attached to plasma membrane. |
| 34 | Second layer (diffuse layer). |
| 36 | Positive and negative ions in diffuse layer. |
| 38 | Third layer (hCG layer). |
| 40 | Negative charges of SIA. |
| 42 | Repulsed or attracted cations in third layer. |
| 44 | Metal ball of the electroscope. |
| 46 | Metal rod of the electroscope. |
| 48 | Metal leaves of the electroscope. |
| 50 | Isolating material or gasket. |
| 52 | Glass container of the electroscope. |
| 54 | Negative or positively charged body or ion. |
| 56 | Electrons. |
| 58 | Electron transfer. |
| 60 | Curve of ABA uptake. |
| 62 | ABA uptake concentrations in percents. |
| 64 | Values of ph between 3 and 8 in a medium outside plasma membrane. |
| 66 | Area of ABA uptake maximum efficiency for inducing stomatal closure. |
| 68 | Area of ABA uptake maximum efficiency for inducing stomatal opening. |
| 70 | pK of ABA (4.7). |
| 72 | Values of pH between 4 and 7. |
| 74 | Relative concentrations of carbonic acid ($H2CO3$) ranging between 0 and 100%. |

| REFERENCE NUMBERS | |
|---|---|
| 76 | Relative concentrations of HCO3 (bicarbonate) ranging between 0 and 100%. |
| 78 | pK of carbonic acid (6.1). |
| 80 | Curve of a buffer solution. |
| 82 | Region of maximum buffering capacity. |
| 84 | Normal blood pH. |
| 86 | ABA optimum extracellular range of pH for inducing cell normalization. |
| 88 | ABA optimum extracellular range of pH for inducing apoptosis. |

DETAILED DESCRIPTION OF THE INVENTION

ABA in Relation to the Human Chorionic Gonadotropin

Dr. Livingston postulated in her U.S. Pat. No. 3,958,025 (1976), col 8, line 50, that a hormone immunologically identical to hCG denominated Microbic Chorionic Gonadotropin, produced from Progenitor cryptocides, might be opposed or neutralized by a growth retardant in vitro. Such a growth inhibitor was identified as ABA.

Experiments in vivo of Dr. Livingston, mentioned in her patent (col 9), demonstrated capacity of ABA to neutralize hCG. For determination of cancer survival rate, she used C57BL/6J mice and C 1498 transplanted tumor with myeloid leukemia purchased from the Jackson Laboratory in Maine. This type of cancer was lethal in mice in 10-15 days. ABA furnished by Hoffmann-Laroche was suspended in saline and administered as suspension. Groups of 10 mice were used for treatment for a total of 7 days.

The following rate of survival was noted at the end of 14 days: Group I: control saline intraperitoneal (i.p)=3 survivors; Group II ABA 1 mg/kg (i.p)=9 survivors; Group III ABA 10 mg/kg (i.p)=10 survivors; Group IV ABA 10 mg/kg (oral)=6 survivors; Group V ABA 100 mg/kg (oral)=9 survivors.

It was concluded that ABA has a marked effect in the inhibition in mice (C57BL/6J) of the tumor system (C1498).

In 1984, Dr. Livingston obtained, pp. 15-38, after treatment of 62 random cases in humans with cancer a success rate around 82%, not considering it inconclusive cases. She applied only a digestive treatment with ABA plus an elimination of the bacterium *P. crytocides* with her vaccine.

Since 70 years ago, *Agrobacterium tumesfaciens* was identified as the cause of crown gall disease which is characterized by formation of neoplasm (galls) in plants. Beijersbergen et al. 1992, p. 1324, determined that such bacterium causes the disease by a DNA transfer. Some others bacteria have been found in plants causing the cancer disease: *Pseudomonas syringae* subsp. *savastanoi* (in olive and oleander) and *Erwinia herbicola* pv. gypsophilae (in *gypsophila*), cited in Ullrich C. I et al. 2000.

Actually it is recognized that, bacteria are not the only agents for inducing cancer; viruses, chemical compounds (toxins), physical elements such as prolonged exposition to solar radiation and other factors can provoke the disease.

Appearance of hCG in tumor cells, induced or not by a specific agent as bacterium or it occurring in placenta or membranes of sperm cells, is a natural mechanism for protecting foreign cells against the immune system of a host organism. hCG is a sialoglycoprotein hormone produced by the human placenta having by function maintenance of the steroid hormone secretions of the corpus luteum and protecting the embryo and fetus against the immune system of the mother. A medicine against cancer must have a fundamental property of counteracting hCG to facilitate viability of tumor destruction by the immune system.

hCG is a glycoprotein containing oligosaccharides. The hormone is composed of two subunits, alfa and beta subunits, having a total of 244 amino acids and forming a complex associated to the cellular membrane.

According to Acevedo 2002, pp. 135-136, alfa subunit contains two chains of n-linked oligosaccharides attached to aspargine with two molecules of n-acetyl-neuraminic acid, known as SIA (FIG. 2). The beta subunit contains four chains of o-linked oligosaccharides attached to the four serines of the hCG beta carboxy-terminal peptide with a total of six molecules of SIA.

The high content of SIA gives the membrane-associated hCG molecule a very high negative charge. SIA appears to be the regular components of all types of mucoproteins, mucopolysaccharides and certain mucolipids.

Cells from the human immune system express in their membranes, normal negative charges. Equal polarity of hCG and immune system cells make such cells immunologically inert and unable to get close and attack tumor cells (Acevedo 2002, p. 136). Specific inhibition of human natural killer cell by SIA and sialo-oligosaccharides has been researched by Van Rinsum et al. 1986, and published through the International Journal of Cancer, vol 38, pp. 915-922.

In addition to the mentioned cancer blockage created by repelling charges against immune cells, hCG also stimulates malignant growth which is summarized in the abstract 227 of Raikow et al. 1987, p. 57, issued in the Annual Meeting of the American Association for Cancer Research.

Others researchers as Stern et al. 1999, p. 367, have related increased negativity in cancer cell plasma membrane with a loss of electrons and protons toward extracellular space. This loss of electron/proton homeostasis and reversion to a glycolytic state are esteemed the basis of their proposed model of carcinogenesis. In this model, DNA abnormalities are considered "contributory or secondary phenomena".

ABA in Relation to Metabolism and Transport of Cations in Cancer Cells

According to Van Slyke 1933, p. 184, from one third to three-fourths of the mineral base in the cellular cytoplasm in normal cells must be neutralized by complex acids, chiefly the proteins and the phosphatides, which are alike in being buffers and indiffusible colloids. Bases such as $K^+$ and $Na^+$ are anchored in the cells in which they form components.

According to A. Keith Brewer 1984, p. 1, in his research named, "The High pH Therapy for Cancer, Test on Mice and Humans", mass spectrographic and isotope studies have shown that $K^+$, $R^+$ and specially $Cs^+$ are most efficiently taken up by cancer cells. Elements such as $K^+$ exert important functions in cancer cell, as e.g., it transports glucose into the cell (Brewer 1984, p. 2). $K^+$ is also important in actively proliferating growing tissues such as embryonic and cancer cells (Delong et al. 1950, p. 721).

Despite above mentioned statements about $K^+$, cancer cells have lower $K^+$ concentrations and higher $Na^+$ and water content than normal cells (Cone, 1975). Likewise, Seeger et al. 1990, cited in Haltiwanger 2003, p. 9, in the monograph, "The Electrical Properties of Cancer Cells", sustains that cancer cells have altered their membrane composition and permeability. This results, in movement of $K^+$, $Mg^{2+}$, and $Ca^{2+}$ out of the cell, and accumulation of $Na^+$ and water inside. According to Brewer 1984, $K^+$ transports 7 water molecules and $Na^+$ transports 16 water molecules. $Na^+$ accumulation in cancer cells brings an additional increase of water. It changes metabolism, physical size, and form of cell. Carcinogenesis causes that, original normal cell gets a round shape because an excess of water.

Apparently, cancer cell malignant transformations have caused a differential preference of cations in relation to the negative charges concentrated in surfaces of the intracellular protein matrix.

G. N. Ling initiated this line of investigation about mentioned above differential preference of cations in cancer cells in the 1960's (Cope, 1978, p. 466), who called it the association-induction hypothesis. Cope called such phenomenon the tissue damage syndrome, because damage in any tissue, produces a similar set of changes in salt and water content. According to Ling 1960, proteins of cells are able to exist in either of two different configurational states: a normal configuration, and a damaged configuration. In a normal state, negatively charged sites on the protein matrix have a large preference for association with $K^+$ rather than $Na^+$, and cell water is highly structured. The result is high cell $K^+$ and low cell $Na^+$. In the damaged cell, proteins lose preference for association with $K^+$ rather than $Na^+$, also they lose their ability to structure water, with the result $K^+$ leaves the cell, and is replaced by $Na^+$, and the water content of the cell increases. Recent studies of cation-specific interactions with protein surfaces have indicated strong preference of $Na^+$ over $K^+$ binding to surface of phosphates and carboxylate groups (Hess et al. 2009). It means that $Na^+$ must be actively pumped out of the cell to: keep an osmotic balance inside and outside of cell, preserve a cell aerobic metabolism and maintain a cell normal configuration state. Inhibition or activation of the $Na^+$—$K^+$ pump ATPase enzyme plays a significant role in a determined presence or preference of those cations in normal or cancer tissue.

On the other hand, $Ca^{2+}$ in cancer cells is contained only at about 1% of that in a normal cell (Brewer 1984, p. 2). Likewise, Delong et al. 1950, p. 718 and Ambrose et al. 1956, p. 576, reveal that, tumor tissues show a decreased $Ca^{2+}$ content in comparison with normal tissues. According to Brewer, $Ca^{2+}$ transports oxygen into the normal cell. ABA increases $Ca^{2+}$ in cytoplasm being taken from the extracellular medium. $Ca^{2+}$ and oxygen increase in cell has a direct connection to the phenomenon of apoptosis.

Limited absorption of $Ca^{2+}$ is another cause of the anaerobic metabolism of cancer cells pointed out by Warburg 1925, p. 310. Cancer anaerobic metabolism is exclusively supported by the biochemical mechanism of glycolysis. It degrades glucose from the blood producing lactic acid and alcohol. An anaerobic cell can only produce two ATP'S from the metabolism of a glucose molecule, while those aerobic cells can derive 36 ATP'S from burning a glucose molecule. That minimal energy provokes: a lack of cellular division and an increased necessity for glucose. It obligates cancer cells to consume bigger quantities of glucose to maintain a reduced state of metabolism, making cancer tissues very addictive to glucose.

ABA as Inhibitor of Alfa-Amylase

This hormone is also able in plants to inhibit enzymes as alfa-amylase blocking hydrolysis of starch and interfering in supplies of glucose. Milborrow 1967, concluded that ABA might be the major component of inhibitor-beta. Likewise Hemberg et al. 1961, pp. 861-867, showed that such inhibitor-beta identified by Milborrow 1967, as Abscisin II suppressed an activity of alfa-amylase, but only insignificantly affected an activity of beta-amylase in resting potato tubers. In addition, Manfield 1971, p. 147, suggested that a starch disappearance in guard cells occur simultaneously with K+ entry. Hence, during stomatal opening ABA is inactivated, not showing any effect on alfa-amylase. Likewise, during stomatal closure aba inhibits alfa-amylase. According to Zeevaart Jan A. D. et al. 1988, page 462, when ABA is applied in barley aleurone layers to 25-fold excess of GA, the synthesis of alfa-amylase, protease, beta-glucanase, and ribonuclease is suppressed. So, alfa-amylase inhibition blocks an available glucose to the cell.

Na+ Mechanisms in Normal Cells

Researches of Cone 1974, clarified a relation between EPD also called electrical transmembrane potential ($E_m$) and associated ionic concentration differences in mitogenesis control of normal and cancer cells.

It has been pointed out that, a cell multiplication or mitosis is stimulated by a cell depolarization. This phenomenon of potential fall is caused by Na+ concentration increase in the cytoplasm.

According to Cone 1974, pp. 423-424, as density of cells increases, a substantial direct cell to cell surface contact begins to develop as well. Hence, a mitotic activity begins to decrease with a corresponding rise in membrane EPD.

Likewise, in order to get a quiescent stage, cells increase membrane EPD by decreasing Na+ concentration in cytoplasm.

In this invention, experiment of Cone 1974, has been interpreted by applying a derivation of the Nernst equation, as follows:

$$EPD[mV]=61 \log [Na^+]e/[Na^+]i.$$

Where, EPD is measured in mV; [Na+] e is an extracellular Na+ concentration and [Na+] i is an intracellular Na+ concentration.

In such experiments of Cone, only Na+ and K+ were measured, therefore in agreement to him, these concentrations could not be directly related to the measured $E_m$ in terms of the EPD. Nevertheless, one ion concentration can be related to EPD, whether it is applied the already mentioned equation according to the concept of Nernst Potential. This concept, considers only one type of ion in a cell, where there would not be any other ions, to know distribution of such ion for a determined amount of potential.

EPD equation is derived from the Nernst Potential equation as it follows:

$$V=RT/zF \ln(Co/Ci)$$

Where V=Nernst Poential in mV; R=universal gas constant (8.314 J/mol.K); T=absolute body temperature (321 K); z=charge on ion; F=Faraday constant (96485.309 C/mol); ln or Log of natural numbers=2.303 $\log_{10}$; Co=concentration outside membrane; and Ci=concentration inside membrane.

In FIG. 3, it is possible to observe a coordinate system, where y-axis is represented by the variable EPD (10) and x-axis is defined by Na+ concentrations in percents (12).

Two curves define a double function. One curve is related to [Na+]i (16). The another one represents to [Na+]e (18). In the upper plane, a depolarization is characterized by an increase in [Na+]i (16) and a decrease in [Na+]e (18). When EPD (10) gets lower values the cell is able to switch from the cell quiescent stage (20) to the cell mitogenesis stage (22).

In Cone's investigation 1974, pp. 423-425, it can be observed Na+ and K+ concentrations (mcmol/ml) in the mitogenesis stage (log phase) and the quiescent stage (saturated) for the used types of normal cells (CHO and 3T3). Values of EPD varied between −10 mV in mitogenesis stage and −65 mV in quiescent stage.

Experimental results by Cone 1974 are shown in the next table:

| ION | CHO MONOLAYER CELLS | | 3T3 MONOLAYER CELLS | |
| --- | --- | --- | --- | --- |
| | MITO-GENESIS | QUIESCENT | MITO-GENESIS | QUIESCENT |
| Na+ | 15.3 +/− 1.8 | 7.9 +/− 2.1 | 17.6 +/− 1.5 | 8.6 +/− 0.8 |
| K+ | 186.1 +/− 5.3 | 185.9 +/− 6.2 | 204.5 +/− 3.6 | 197.0 +/− 4.8 |

It may be seen in the cone experiment results that a significant variation occurs in Na+, but not in K+. That means, it is Na+ the ion really involved in cell mitogenesis control.

At this point it is necessary to recall that, ABA is able to produce seed dormancy and growth inhibition in plants (see paragraphs [0009] and [0010]) and also growth inhibition in animal cells. Therefore, it is evident and suggests that the cell hyperpolarization and decrease of [Na+]i in cancer cells induced by ABA, could be effects conducting cells to get a quiescent stage.

Thus, EPD and Na+ concentration changes, outside and inside of cell, are provoked and dependently related to, which Na+ transport system is activated and which one is inhibited. During the quiescent stage, normal cells depend of Na+—K+ pump ATPase enzyme. This enzyme mediates the transportation of 2 K+ going into the cell for 3 Na+ going out of cell with the consumption of 1 ATP molecule in the process. Nevertheless, when a cell triggers mitosis a secondary transport system is activated. According to Mahnensmith et al. 1985, normal cells contain a secondary transport system that mediates the transmembrane exchange transport of Na+ for H+. It is also revealed in this research that, this secondary system plays among other, a physiological role in cell growth and proliferation.

Na+ Mechanisms in Cancer Cells

Cone 1974, p. 431, remarked that "a cancer cell multiplication or mitosis is characterized by a sustained and pronounced cell depolarization in conjunction to an increase of Na+ concentration in the cytoplasm. This phenomenon of malignant proliferation blocks or negates the effective functioning of the ionic regulatory system resulting in a sustained cell depolarization with associated inability to lower the Na+ concentration to nonmitogenic levels. That cancer cell inability to decrease Na+ would be associated to a reduction of the effective operation of Na+ pump". In cancer cells, Na+—K+ pump ATPase Enzyme is inhibited and it remains as unable to be reactivated. It reduces the entry of K+ and exits of Na+. The secondary system (Na+—H+ exchanger) already mentioned is activated; according to Mahnensmith et al. 1985, this alternative secondary system plays also a pathophysiological role in diverse conditions such as cancer, renal acid-base disorders, hypertension and tissue and organ hypertrophy. Herein, it is possible to state that the Na+—K+ pump ATPase enzyme is associated to the hyperpolarization condition of normal cells and the secondary antiport system is correlated to the depolarization condition of cancer cells.

Electrical changes such as, lower EPD in rapidly proliferating and transformed cells, have been reported by Binggeli et al. 1986; it has also been reported by Marino et al. 1994, specifically in breast cancer, and reported by Davis et al. 1987 and Goller et al. 1986 in colon cancer.

In agreement to aforesaid statements, cancer cells are not able to switch to a quiescent stage, which provokes in such cells a perpetual and uncontrolled cellular proliferation.

Sustained depolarization in cancer cells can be considered a deviated variant of the general mitogenesis model of normal cells as observed in FIG. 3. ABA action is capable to abort the malignant mechanism by shifting cancer cells from a depolarized and damage configurational state to a hyperpolarized and normal configurational state.

Modified Triple Layer Model

Figure 5:
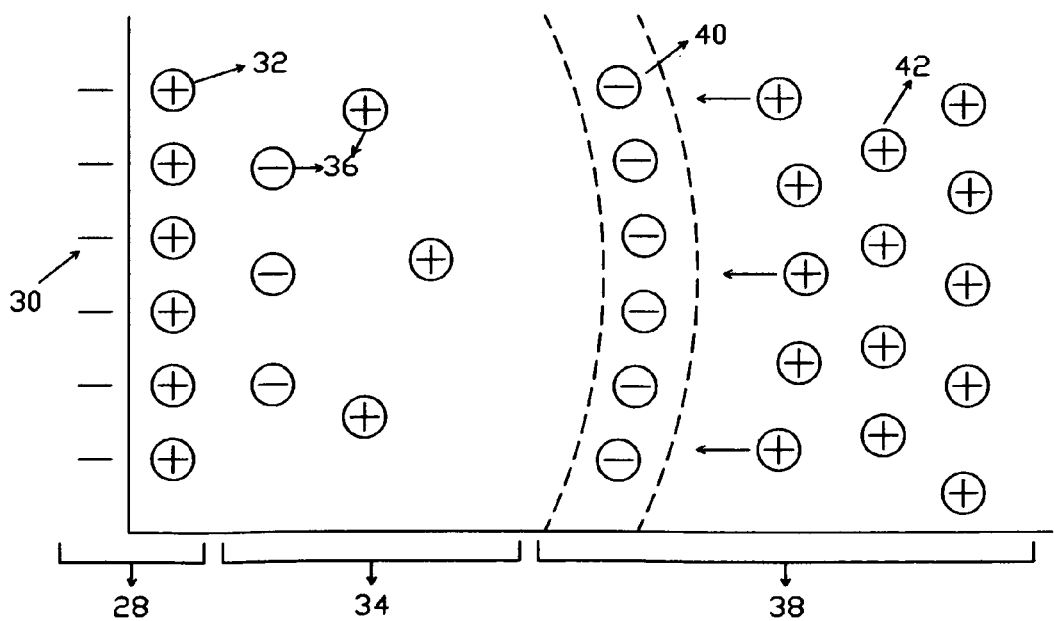
FIG. 5 is an illustration of the concentration gradient of $Na^+$ toward the cell.

Presence of membrane-associated hCG molecule of cancer cells determines theoretically, according to this invention and FIGS. 4 and 5, a variation of the triple layer model. Three fundamental layers structure this model. They are:

1. A first layer (28), the innermost or surface layer, also called the Stern layer, which consists of the plasma membrane's solid surface itself with negative charges (30) and local positive ions (32).

2. A second layer (34) or diffuse layer defined by adsorbed negative and positive ions of relatively strongly bound (36).

3. A third layer (38) or hCG layer, consisting of SIA negative charges (40) in the hCG outer glycocalyx, plus adsorbed or repelled cations (42).

Many models have been developed which explain the behavior of a membrane. The diffuse double layer designed by Gouy (1910), the Stern model, the Gouy-Chapman-Stern-Grahame electric double layer and the triple layer model have widely been studied.

Original triple layer model in normal cells consists of a diffuse third layer with ions weakly attracted to the solid surface. This triple layer model in this invention is modified due to the presence of hCG in cancer cells, which makes tumor cells behave in an atypical fashion. It functions in cancer cells, as an electrical barrier 20 microns far from the Stern layer. There, negative charges (40) exert the important role of repelling cells of the immune system and serve apparently also as receptors.

Absorption of substances by the plasma membrane can be considered an electrostatic mechanism, where diffusing mechanisms are also involved. An hCG barrier produces an additional compartment area, which can be used by cancer cell to handle adequate ionic concentrations close to the plasma membrane and produce favorable concentration gradients toward or from the cytoplasm.

For example, low $Na^+$ concentrations in first and second layers (28) and (34) are able to produce a concentration gradient between the third layer (38) and these inner layers (FIG. 5). Thus, $Na^+$ can be efficiently diffused to inner layers and subsequently to the cytoplasm.

ABA as Tool for Changing Polarization of hCG

Cations can be involved in binding to SIA. Tiralongo 2002, p. 4, mentions in the apart of biological roles of SIA that, due to negative charges, SIA are involved in binding and transport of positively charged molecules, as e.g. $Ca^{2+}$. According to Delong et al., 1950, p. 718 and Ambrose et al. 1956, p. 576, cellular surface of cancer tissues shows a decreased $Ca^{2+}$ content in comparison with normal tissue. $Ca^{2+}$ deficiency has been associated to linking decreased adhesiveness and invasiveness of cancer cells.

Cations such as $Ca^{2+}$ and $Mg^{2+}$ are deficient in cancer tissues. Its outside transport is not able to produce important changes in EPD. In malignant tissues the $Na^+$—$H^+$ antiport system is activated, and it regulates $Na^+$ import to the cell and $H^+$ export from it. Thus, $Na^+$ becomes the most important cation cell inside; although $K^+$ is contained in smaller amounts, cation exportation of both could change negative charges of hCG, because a transport of such cations exerts drastic changes in EPD. ABA can be medically used in humans as an ion exporter, because it has a capability for moving these cations to the outside of plasma membrane. $Na^+$ concentration gradients reversed toward the ECF have been found in relation to a cancer patient curative process. The efflux direction is defined by higher concentrations of $Na^+$ contained in first and second layers (28) and (34) and lower concentrations contained in third layer (38), (FIG. 4).

According to clinical observations of Dr. Max Gerson, when cancer patients were responding to treatment, they lost extra $Na^+$ from the body in the urine (Gerson M 1978, p. 454, Cope F. W 1978, p. 466). These observations of Dr. Gerson are clearly indicative that, an excess of $Na^+$ is eliminated from patient body during the process of cancer recovery and, $K^+$ is not.

According to Dr. Gerson the other part of the human body recovery process from cancer disease was replacement of excess $Na^+$ by $K^+$ in damaged tissues. Those results obtained and developed by Dr. Gerson during 30 years of clinical experimentation are found correlated to thesis of Ling 1960, and, Cope 1978, about the association-induction hypothesis and tissue damage syndrome (see paragraph [0069]). Extruded $Na^+$ and regained $K^+$ are effects or consequences of a change of cancer cell configuration state, in which the malignant cell switches from a damage configuration state to a normal state. There, after malignant mechanism is aborted, $Na^+$—$K^+$ pump is activated and cell regains presence and preference for $K^+$.

Healthy cell is associated with higher intracellular $K^+$, lower intracellular $Na^+$ and higher EPD, and cancer cell is associated with lower intracellular $K^+$, higher intracellular $Na^+$ and lower EPD (Cone 1975, cited in Haltiwanger 2003, p. 30). At this point it is possible to predict that, membrane potential (EPD) is the essential factor for switching from a damage configurational state to a normal state. A variation (increase) in EPD, inexorably conducts in cancer cell toward a normal configurational state.

ABA exporting both cations to the cell outside provokes a membrane hyperpolarization, which aborts mentioned profound and sustained cancer cell depolarization. $K^+$ high mobility and $Na^+$—$K^+$ pump ATPase enzyme activation will facilitate that, $K^+$ can be regained by cancer cell cytoplasm.

In agreement to Haltiwanger 2003, p. 41, some effects that are seen when membrane potential (EPD) is increased include: enhanced cellular energy production (ATP), increased oxygen uptake, changes in entry of $Ca^{2+}$, "movement of $Na^+$ out of the cell, movement of $K^+$ into the cell", changes in enzyme and biochemical activity, and changes in cellular pH.

It is believed in this invention that, ABA ion decrease will produce a hCG positive polarization, which is accomplished through an electron removal from hCG outer layer, toward cancer cell cytoplasm.

This last statement denotes that, a plasma membrane subtle electrostatic phenomenon might be exerted by ABA hormonal action.

Electrostatic Phenomenon in Plasma Membrane, Redox Reaction, Electrical Equilibrium, Electron Depletion and Reorganization of Charges According to a large number of researchers, total cell structure is connected through a liquid crystal protein polymer connective system continuum. This term has been used to express that, such system connects the cytoskeletal elements of the inside through cell membrane, as a total structure. Haltiwanger 2003, p. 20, reveals that such a continuum of liquid crystal connections in cells, deeply studied by Becker 1974, Ho MW 1998, and, Oschman J. L 2000, allows electrons and photons to move in and out of cells. In his opinion, "cytoskeletal filaments" function as electronic semiconductors and fiberoptic cables integrating information flow, both within the cell and with other cells. Also it is believed that, cytoskeleton proteins link the inside of cell like a system of telegraph wires terminating onto the nucleus membrane (Ho 1993, p. 94), or act as coherent molecular antennas radiating and receiving signals (Oschman J. L 2000, p. 131).

Dr. Merrill Garnett 1998, has studied for decades the charge transfer role and electrical current flow in the cell. He believes that DNA, cytoskeletal proteins and cell membranes transmit an inward and outward current. The inward current flows from the cell membrane to cell structures like mitochondria and DNA, and, the outward current flows back along liquid crystal semiconducting cytoskeletal proteins through the cell membrane to the extracellular matrix.

Nature of cellular electron movement in transport systems as it occurs, for example in mitochondria and chloroplasts has been well known, but outside transport systems is poorly understood (Stern et al. 1999, p. 368). Certain theories have been proposed. Through a total cell, electrical transmission must flow on protein surfaces. According to Adey 1988, p. 149, electrical interactions between cell membrane and weak electromagnetic fields are exerted through electrical charges located on cell surface macromolecules. Proteins and macromolecules function as semiconductors (Szent-Gyorgyi A 1978,85, Brillouin L 1966). In addition to semiconductivity, complex crystalline structures possess properties such as photoconductivity and piezoelectricity (Becker 1999, p. 237). In proteins, at a specific level, a passage of electrons is produced through a major cytoskeletal component (actin) by which ionic currents are induced. Cytoskeletal structures can behave as electrical wires and are capable of functioning as nonlinear inhomogeneous transmission lines (Lin E et al. 1993, cited in Stern et al. 1999). Concentric and structured water surrounding proteins must also interact as dipole conducting electrical currents.

When $Na^+$ and $K^+$ are exported outside of cancer cell by ABA action, it occurs an electrical attraction by coulombic forces between cations and hCG negative charges. Those negative charges are found distributed along hCG filaments in extra and intracellular space. Therefore, such pairs of coupled positive and negative charges produce a small charge difference, prompting an electrical current through hCG filaments. This "transient coupling" of positive and negative charges is the phenomenon of the same described and experimentally proven in vitro by Dr. Virginia Livingston, which she defined as the neutralization of the Microbic Chorionic Gonadotropin. (see paragraph [0037]).

Redox Reaction

Those pairs of coupled charges work like generators. In electrical generators the current is driven by the potential difference or voltage. Thus, there is established an electrical field. In generators, the electrons are transferred from the negative pole toward the positive pole, through the conductor, which unifies both poles. Inside of generators and to complete the circuit, electrons are transferred from the positive pole toward the negative pole. This internal electron transfer produces the necessary electric energy. In hCG filaments water is the conductor. In normal cells the electrical current travel through a pattern of water concentric rings; in cancer cell presence of $Na^+$ produces loss of this pattern.

Electricity is a universal phenomenon. So, in general sense certain biological cellular structures have a similar behavior to electrical or electronic components. In plant and animal tissues, electricity must flow under the same concepts and laws as it does in electrical or electronic components. In cancer tissue, when cations are exported to the cell outside and such cations confront hCG negative charges, they form ionic bonds along filaments. It produces an electrical potential difference or voltage. This mechanism drives electrons from a SIA negative charge (40) in third layer or hCG layer (38) toward the nearest ionic bond down road where that confrontation happens. According to the electroscope device, attraction of positive and negative charges prompts an electrical current (see FIG. 7). Thus, such charge confrontation in water produces an electrolyte double redox reaction between the polyatomic ion [SIA-COO]$^-$, which works as a cathode and the cation [Na]$^+$, which works as an anode. As water is the conductor and electrical current comes through, electrolysis is the phenomenon involved. These coupled charges immersed with water generate a electrical circuit and may be considered redox centers:

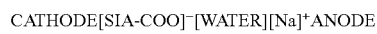

CATHODE[SIA-COO]$^-$[WATER][Na]$^+$ANODE

In this case, the anode is formed because, in ABA induced cation exportation from cancer cells, $Na^+$ will be the predominant cation. Likewise, in tumor cells the cathode represents the SIA negative charge which is found in the carboxil group (See FIG. 2).

[Na]$^+$ as oxidant having an electronic distribution (2,8), is reduced by winning one electron, and, [SIA-COO]$^-$ as reductant is oxidized by loosing two electrons. Both reactions are electronically compensated and 2$e^-$ is the transferred net charge between both electrodes, as it follows:

$$2[Na]^+ 2e^- \rightarrow 2Na \quad \text{(1) ANODE REDUCTION}$$

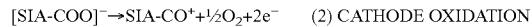

$$[SIA-COO]^- \rightarrow SIA-CO^+ + \tfrac{1}{2}O_2 + 2e^- \quad \text{(2) CATHODE OXIDATION}$$

In electrolysis, hydrogen is evolved at the cathode and oxygen is evolved at the anode, thus water is reduced to form hydrogen and oxidized to form oxygen, as follows:

$$2H_2O \rightarrow O_2 + 4H^+ + 4e^- \quad \text{(3) ANODE OXIDATION}$$

$$4H_2O + 4e^- \rightarrow 2H_2 + 4OH^- \quad \text{(4) CATHODE REDUCTION}$$

Herein double redox reaction happens. In the anode the half reactions (1) and (3) interact and in the cathode reactions (2) and (4) do the same as follows:

$$2Na^+ + 2H_2O \rightarrow 2Na + O_2 + 4H^+ + 2e^- \quad \text{(5) ANODE}$$

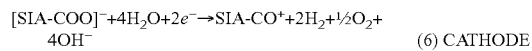

$$[SIA-COO]^- + 4H_2O + 2e^- \rightarrow SIA-CO^+ + 2H_2 + \tfrac{1}{2}O_2 + 4OH^- \quad \text{(6) CATHODE}$$

In reaction (5) the anode gains two electrons from the water and loose them, which are transferred to the cathode in reaction (6). The reactions (5) and (6) combine and exchange components as follows:

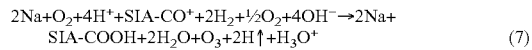

$$2Na + O_2 + 4H^+ + SIA-CO^+ + 2H_2 + \tfrac{1}{2}O_2 + 4OH^- \rightarrow 2Na + SIA-COOH + 2H_2O + O_3 + 2H\uparrow + H_3O^+ \quad (7)$$

In reaction (7) SIA-CO$^+$ is reduced by one hydroxide to form the carboxyl group; 4H$^+$ and 3 hydroxides form two water molecules and one H$_{30}{}^+$. Also one diatomic oxygen molecule (O$_2$) and one oxygen atom ($\tfrac{1}{2}$O$_2$) react to form ozone (O$_3$). The ozone in contact with water gives up its extra atom of oxygen, which is not bonded very tightly, and connects up with water to produce the reactive oxygen specie—hydrogen peroxide, as follows:

$$H_2O + O_3 \rightarrow H_2O_2 + O_2\uparrow \quad (8)$$

Final components of reaction (7) keep an acid-base ionic balance according to theory of bronsted and lowry (acid gives a proton and base accepts the same proton). Thus, it is established an ionic equilibrium between dissociated and non-dissociated components, according to simplified reaction (9).

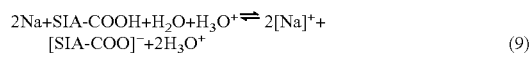

$$2Na + SIA-COOH + H_2O + H_3O^+ \rightleftharpoons 2[Na]^+ + [SIA-COO]^- + 2H_3O^+ \quad (9)$$

Although SIA-COOH is a weak acid, complementary acidity and delocalized charge that stabilizes the conjugate base makes that acid stronger and shift the equilibrium to the right. Both the carboxyl acid group and the carboxylate anion (conjugate base) are stabilized by resonance, but the stabilization of the anion is much greater than that of the carboxyl group. It may also be observed in reaction (9) that one [SIA-COO]$^-$ reacts with two [Na]$^+$. Such characteristic might be owing to that, the negative charge of the carboxylate anion [SIA-COO]$^-$ is delocalized over both oxygen atoms to form a stable resonance hybrid. Research of Hess et al. 2009, page 13299, points out that small ions with a high surface charge density as ($Ca^{2+}$ and $Na^+$) pair up with major intracellular anions such as (phosphates and carboxylates). Contact ion pair between $Ca^{2+}$ (with double valence) and carboxylate must be exerted by attraction to both oxygen atoms of the anion, which shares the negative charge.

If charge confrontation happens in another redox center down road, the polyatomic ion [SIA-COO]$^-$ will loose two electrons as expressed in reaction (2). It will produce a positive polarization of the hCG-membrane associated molecule and a release of [Na]$^+$:

[SIA-CO]$^+$DISSOCIATION[Na]$^+$

According to P. L Dutton et al. 1999, in the research "How Biological Molecules Move Electrons: Simplicity Trumps Complexity", electron transfer occurs between redox centers within proteins and it is accomplished by means of an instantaneous quantum mechanical phenomenon called tunneling. Also according to Tezcan et al. 2001, electron transfer in proteins involves as a third step a dissociation of the oxidized and reduced products. Electron loss from the carboxilate anion in reaction (9) or (2) may supply a net charge of two electrons to activate another redox center. The dynamic of the process is given by an electron transfer cycle that, it will switch off a protein segment up road, and, switch on a protein segment down road. Finally, in reaction (8) one molecule of hydrogen peroxide is produced. According to Zhang et al., 2001, many metabolic processes, including chloroplastic, mitochondrial, and plasma membrane-linked electron transport systems, produce ROS such as the superoxide radical ($O_2^-$), the hydrogen peroxide ($H_2O_2$), and the hydroxyl free radical (OH$^-$).

Electrical Equilibrium, Electron Depletion and Reorganization of Charges

Energizing stages or generators will conduct the current to a cell area with bigger electron deficiency. In order to obtain the cell an electrical equilibrium, the most electron probable destiny could be the cancer cell cytoplasm. According to Stern et al. 1999, malignant cell metabolism works as pumps of protons and electrons, coming from cytoplasm and going out to increase electronegativity of the extracellular space (see paragraph [0064]). They also mention that, a constant flow of electrons from cytoplasm finally it causes cancer cell electron depletion.

The electron transfer directed to the cancer cell cytoplasm will increase the cell energy and EPD. These effects might reactivate the $Na^+$—$K^+$ ATPase enzyme, permitting it $K^+$ reentry toward the cytoplasm.

Tsong T. Y 1989, and, Blank M 1987, mention that, ion accumulation near the membrane surface has been shown to reproduce some results with the $Na^+$—$K^+$ ATPase enzyme. It also is mentioned by Tsong T. Y in this research that, $Na^+$—$K^+$ pump enzyme is shown to utilize free energy transmitted through an oscillating electric field to pump $Na^+$ and $K^+$ against their respective concentration gradients.

Another effect produced by the electron transfer would be, the transient conversion of hCG negative charges in positive charges. When electrons are ejected to the cancer cell cytoplasm, it will produce in each pair of coupled charges in redox centers, a cation reject and ion movement by coulombic forces along hCG filaments. Polarized hCG positive charges can not longer attach cations. It will conduct $Na^+$ excess to the bulk and $K^+$ returning to the cell. The end of this chain reaction, produced by ABA, may be found in connection to theory of Dr. Max Gerson.

As $K^+$ returns to the cell, a change of configurational state occurs, from the damage to the normal. Likewise, as cancer cell becomes in normal, hCG is inhibited and cell recovers its original negative charge. In conclusion, during a process of cell normalization or differentiation, what it accounts is just an electronegativity reduction of the cell surface charge. The master thesis of M. E Kruse made in 2006 reported a reduced luminescence (indicator of reduced negative surface charge) by ABA effect in four humans cancer cell lines. She assumed and attributed it to a reduced cancer cell proliferation.

The electroscope is a device, which transmits electrical currents such as it could occur through cell filaments and structured water.

The Electroscope Device

Haltiwanger 2003, p. 6, has cited that there are multiple structures in the cell acting as electronic components due to that, biological tissue and components can receive, transduce and transmit electric, acoustic, magnetic, mechanical and thermal vibrations. For example, membrane proteins and DNA consist of helical coils. These structures function as electrical inductors (Haltiwanger 2003, p. 5). Cell membrane functions as a capacitor with leaky dielectric characteristics (Garrison W, 1969).

Nobel prize winning Szent-Gyorgi A, resembled cell membranes as closely analogous to the PN junction, a semiconductor device used in solar cells, which facilitates a positive and negative charge separation and is capable of generating an electric current when excited by heat or light (Ho 1993, p. 102).

The electroscope device, which determines or measures presence of electrostatic forces has a strong correlation to the electron transfer theory in liquid crystal continuum system of the cell. Two different directions follow up the electron movement across the plasma membrane. One direction is induced by the phenomenon of ion decrease and the another opposite direction is induced by the phenomenon of ion absorption. It has already been mentioned, between the paragraph [0115] and [0124], the induced mechanism of ABA "ion decrease" in cancer cells. If one cation as $Na^+$ or $K^+$ is exported outside of plasma membrane, one electron comes back to the cell in order to restore both, the cell electrical equilibrium and the cytoplasm electron depletion. Nevertheless, in ion absorption phenomenon the electron transfer direction is complete opposite.

Figure 6:
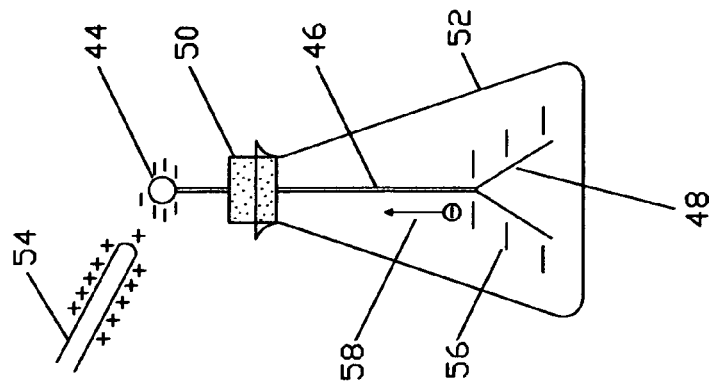
FIG. 6 is an illustration of the electroscope in contact with a negatively charged body.
Figure 7:
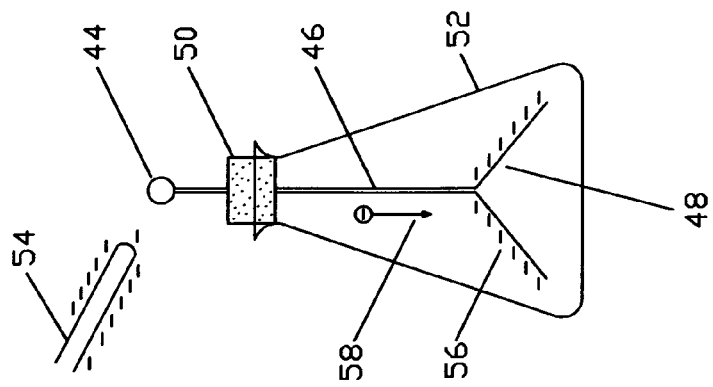
FIG. 7 is an illustration of the electroscope in contact with a positively charged body.

In graphic 6 and 7 of this invention, can be observed two identical electroscopes in contact with negative and positive charged bodies. Several elements of the electroscope device have a similar element in normal and cancer cell plasma membrane, according to the following similes: the metal ball (44) can be considered SIA receptors showing plasma membrane negative electric charges in inner and outer layers. The metal rod (46) can be considered glycoprotein projections coming from the membrane-associated hCG molecule. The metal leaves (48), likewise, can be considered the plasma membrane and $Na^+$ channels. The negative and positive charged bodies of the electroscope can be considered ions as, for example $Na^+$ (54). The electron (56) and the electron transfer (58) have no simile, because they are naturally identical. The electroscope glass container (52) and gasket (50) can be considered the plasma membrane lipid bilayer isolating properties. In FIG. 6, if it is approached to the metal ball (44), a negatively charged body (54), for example a frictionally resin rod, some electrons (56) are transferred (58) through the metal rod (46) toward the extreme of the device where the metal leaves (48) are. Such metal leaves (48) will widely open due to coulombic forces, which repel charges of the same polarity. In FIG. 7, if it is approached to said metal ball (44), a positively charged body (54), said metal leaves (48) get closer, due to that electrons (56) are transferred (58) to the metal ball (44). Likewise if this metal ball (44) comes in contact with the ground, for example, touching it with a finger, some electrons (56) will escape from the electroscope glass container (52).

In malignant tissues, $Na^+$ absorption has been found correlated to electron efflux. According to Stern et al. 1999, page 368, transplasma membrane electron transport is coupled to the $Na^+$—$H^+$ antiport exchange, and electron efflux is associated with proton efflux. It means that, when one ion $Na^+$ is transported to the intracellular space by the antiport system, one proton and one electron is exported to the extracellular space. In normal cells as in cancer cells as well, when a current of cations gets close to the plasma membrane in order to be absorbed, the electron transfer nature follows the electroscope device in FIG. 7. According to it, if a positively charged body (cation) approaches to SIA negatives charges of proteins, electrons escape from cell cytoplasm and plasma membrane, causing it a depolarization. The following statements explain in detail, these electron transfer phenomenon implications.

Depolarization of Plasma Membrane Caused by Ionic Currents

A model developed by Tsong 1989, has postulated that a protein can undergo conformational changes by a coulombic interaction with an oscillating electric field.

It is possible to assume that, cation attraction to negative charges of sialoglycoproteins, in the plasma membrane and ion channels, can generate electrical changes in such proteins.

Study of the elctroscope device can suggest that, electron transfer may also occur from the plasma membrane to currents of cations causing a removal of negative charges (electrons) in cell membrane and ion channels. When said electrons are removed, conformational changes happen in the plasma membrane, most importantly a depolarization.

According to Bennett et al. 1997, in an article titled "Contribution of Sialic Acid to the Voltage Dependence of Sodium Channel Gating. A Possible Electrostatic Mechanism", changes in $Na^+$ ion channel of rat skeletal muscle were observed, after enzymatic action of neuramidase, such as SIA removal. These changes in channels were, 10 mV more depolarized than control channels. Bennett et al. also point out that, a general feature of many $Na^+$ ion channels is that they are heavily glycosylated with a large carbohydrate fraction in the form of SIA. In this mentioned research of Bennet et al. 1997, SIA negative charges removed from ion channel surfaces is found associated to depolarization.

Electrostatic Phenomenon Hypothesis in $Na^+$ Channel.

In aforesaid statements it can be observed that, an interaction between currents of cations and $Na^+$ channel SIA negative charges, may be given through an electrostatic phenomenon.

From a general knowledge, a plasma membrane depolarization effect probably produced by electron removal has a consequence in opening the channel.

Opening and closing ion channels can be interpreted in this invention, through the electroscope device, to eventually demonstrate that electron transfer is the underlying mechanism in plasma membrane ionic interactions.

According to Marban et al. 1998, p. 647, $Na^+$ channels consist of various subunits, but only the principal (alfa) is required for function. The alfa subunit has a modular architecture: it consists of four internally homologous domains (labeled I-IV), each of which contains six transmembrane segments. The four domains fold together so as to create a central pore. According to Stuhmer et al. 1989, the fourth transmembrane segment (S4) stereotypically studded with positively charged residues, lies within the membrane field and moves in response to depolarization, somehow opening the channel. In agreement to Bennet et al. 1997, p. 327, the segment (S4) consists of a repeated triad of two hydrophobic aminoacids followed by a positively charged residue, consistent with a role as a voltage sensor, residing within the membrane bilayer. The rest of the segments of the $Na^+$ channel are negatively charged with SIA. Schematic depictions of the $Na^+$ channel alfa subunit are shown by Marban et al. 1998, p. 648.

According to Catterall, W. A 1992, it is assumed a helix model where each positively charged residue in the (S4) segment is paired with some negative charge on the adjacent S1 to S6 segments (cited in Aidley et al 1996, p. 186). This model appropriately suggests that, coulombic interactions (attraction and repulsion forces) occur between paired negative and positive charges in channels.

On the other hand, Hodgkin and Huxley 1952, found that changes in ionic permeability were associated with the movement of some electrically charged particles within the membrane. Thus, movement of charged particles may be given toward positive charges of segment (S4) or from negative charges of adjacent segments of channels.

Stuhmer et al. 1989, also found that the steepness of the relation between channel opening and the membrane potential was progressively "reduced" as the positively charged residues of the (S4) segment were replaced by neutral or negatively charged residues. This research, automatically realizes that, movement of charged particles mentioned by Hodgkin and Huxley 1952, happens from negative charges of adjacent segments of channels.

In this invention, it is disclosed under the electroscope device standpoint that, cation currents close to the channel will produce a electron removal from the negatively charged segments of the channel, decreasing negative charges in such segments or increasing positive charges in it. At that point, a positive charge is generally expressed by all the segments. When it occurs, segment (S4) is moved away from the rest of the segments due to repelling coulombic forces. Electrons removed from the channel, neutralize said current of cations. Thus, such ions switch from an ionic stage to a neutral or uncharged stage. When neutral particles get across the channel, negatives charges acquired before entering to the pore are incorporated back to the channel. After the process is completed and once electrons get back to adjacent segments during the passage, positive segment (S4) is again attracted to negative segments of the pore. This latter phenomenon produces the closing of ion channel.

The cell membrane lipid structure makes it relatively impermeable to the passage of charged molecules. This well known lipid membrane transport property can be understood as a generalized rule, if charged molecules or ions get across channels as uncharged molecules, according to theoretical gating model expressed in this invention.

Apoptosis by ABA Action

According to Fingrut et al. 2002, from the Tel-Aviv University, plant stress hormones as sodium salicylate (SA), jasmonic acid (JA) and methyl jasmonate (MJ) can suppress the proliferation or cause apoptosis in certain mammalian cancer cells (lymphoblastic leukemia, prostate, breast and melanoma human cancer cells). Although SA, JA and MJ rather hold a secondary role as plant inhibitors, this evidence reveals the power of plant stress hormones against cancer. In this invention, ABA has been correlated to a process of cancer cell normalization. Nevertheless and paradoxically, an apoptosis phenomenon is induced by ABA hormonal action as well. It was experimentally confirmed for first time in cancer cells by Tang et al. 2006, from the Chengdu Biological Institute Academy of Sciences and by Marianne Ehrhorn Kruse, then at the University of Southern Denmark.

In plants and according to Vanyushin B. F et al. 2004, peroxides, ABA, ethylene releaser ethrel, and DNA methylation inhibitor 5-azacytidine induce and stimulate apoptosis. This research points out distint ultrastructural features of apoptosis such as: compaction, vacuolization and fragmentation of cytoplasm in the apoptotic cell; appearance in the vacuole of unique single-membrane vesicles containing active organelles; cessation of nuclear DNA synthesis, and, condensation and margination of chromatin in the nucleus; internucleosomal fragmentation of nuclear DNA; and intensive synthesis of mitochondrial DNA in vacuolar vesicles. According to Tang et al. 2006, from The Chengdu Institute of Biology, ABA produced changes in morphology of cancer cells in DU-145 (prostate cancer) and in HL-60 (promyelocytic leukemia). The results showed: in DU-145 tumor cells (growth in poor condition and nuclear pycnosis) and in HL-60 tumor cells (absence of tumor cell nuclear membrane microvilli and presentation of typical apoptosis characteristics). It was also found in both types of cancer cells that, tonofibril disappeared and number of cell organs were reduced.

It has been held in this invention that, ABA produces unequivocally cancer cell ion decrease. In a cell normalization process caused by ABA, $K^+$ is regained in order to: incorporate lost water, replace charges in proteins and change the metabolism. Nevertheless, during an ABA apoptotic process, $K^+$ uptake is inhibited being it not regained by cancer cell. This phenomenon may be found in connection to production of peroxides during apoptosis. Zhang et al. 2001, demonstrated that potassium channels are inhibited by hydrogen peroxide mediate ABA signalling in *Vicia* guard cells. In the paragraph [0018], it has been mentioned that ABA increases $Ca^{2+}$ uptake. This ion transports oxygen to the cell (Brewer 1984, paragraph [0070]). In addition and according to Schroeder et al. 2001, cytoplasm $Ca^{2+}$ elevation produced by ABA signalling inhibits $H^+$ efflux and $K^+$ uptake (see paragraph [0022]). ABA oxygen uptake and reactive oxygen specie formation ($½O_2$) by electron transport may trigger reactions for producing hydrogen peroxide. It may be also suggested that ROS and peroxides interfere with the re-activation of the $Na^+$—$K^+$ pump. This phenomenon would be part of a cellular process of destruction and fragmentation.

ABA initial effect of $K^+$ and $Na^+$ decrease is exerted without a criterion of selectivity. That means that both of those ions, and not just one in particular, are transported outside of plasma membrane. (see paragraph [0023]).

Ion decrease from cell produces an intracellular water reduction, because $Na^+$ and $K^+$ drag with itself a lot molecules of water, see paragraph [0067]. It reduces volume and size in apoptotic cancer cell and probably also in apoptotic senescent normal cells.

This phenomenon of $Na^+$ and $K^+$ decrease has been found in connection to a mechanism of cell shrinkage in apoptotic cells (Bortner C D et al. 1997, 1998; Gomez-Angelats et. al 2004; Mann C. L 2001; Nukui M et al. 2006).

Specifically and according to Bortner C. D et al. 1997, "$K^+$ and $Na^+$ Efflux" play a primary role in apoptosis activation. Also, in 1998 they mention that, loss of cell volume had been thought to be a passive secondary feature of apoptosis, but it has now become an area of research interest. Likewise, in agreement to Gomez-Angelats et al. 2004, this knowledge may also have an impact on the design of therapeutic strategies for a variety of diseases of the immune system in which apoptosis plays a central role, such as oncogenic processes or immune system disorders.

Although the involved apoptosis signalling molecule has not yet been identified by medical physiologists, ABA is the hormone casually related in producing: apoptosis and also the "Efflux of $Na^+$ and $K^+$". This cell shrinkage phenomenon, which it occurs during induced ABA apoptosis, has technical similarities with the plant stomatal closure mechanism. In stomatal movements the solutes leave and come back to the stomate, therefore, the phenomenon can be turned and reversed depending the plant hydration condition. Apotosis is not a reversible phenomenon.

ABA in Relation to the Immune System

ABA $K^+$ and $Na^+$ efflux from cell is a common phenomenon during ABA cell normalization and apoptosis. ABA cell normalization produces that, those ions "temporarily" remain outside of cell. Under that mechanism, $K^+$ and water return to the cancer cell cytoplasm, transforming the cancer damage condition toward a stage of normal. When the cell gets through an apoptosis process, it is produced $K^+$ uptake inhibition (see paragraph [0146]). If $Na^+$ remains outside of cell and $K^+$ uptake is inhibited, the cell shrinks in an irreversible way. It produces the cell water to get out provoking a cell volume loss or cell shrinkage.

Whether water and ions have been lost, shrinking cell and fragments would turn toward a permanent positive polarization of membrane-hCG associated molecule. This phenomenon may stimulate an attraction between apoptotic cell or its fragments and immune system cells. $K^+$ and $Na^+$ uptake inhibition by cell produces respectively electron inhibition efflux toward the extracellular space. Thus, cancer membrane positive charge, during or after apoptosis, remains unaltered. This well designed and intended mechanism by nature will produce the necessary attraction, between cancer and immune cells. Without ABA, those cells would remain immunologically inert. New investigations about ABA could suggest the real function of ABA as an endogenous cytokine when the hormone is released by human immune system cells.

According to Bruzzone et al., 2007, ABA has been identified as an endogenous cytokine in human granulocytes. They mention that, ABA stimulates several functional activities as phagocytosis, reactive oxygen species (ROS) and nitric oxide production, and chemotaxis of human granulocytes. In agreement to this research, increase of free intracellular ABA and its release by activated human granulocytes indicate that, ABA should be considered as a new pro-inflammatory cytokine in humans. In addition, invention of Zocchi et al. 2008, titled "Fluridone as an Anti-inflammatory Agent" teaches that, by using HPLC-MS analysis, ABA presence was also demonstrated in human lymphocytes, fibroblasts (skin), mesenchymal stem cells (bone marrow stroma precursors), platelets and monocytes.

It has been written in this invention on the paragraph [0062], that equal polarity of hCG in cancer cells and immune system cells make such cells immunologically inert and unable to get close and attack tumor cells (Acevedo H 2002, p. 136). Because theory of Acevedo H is correct, only cancer cells expressing an absolute membrane positive surface charge might be attracted to immune system cells, which express negative surface charge. Partial reduction of a cancer cell surface charge electronegativity would not be enough to induce the proximity.

Considering the investigations of Bruzzone et al. 2007 and invention of Zocchi et al. 2008, it may be suggested, that ABA must be used by immune cells for producing a strict order of two consecutive events. First: to change the polarity of hCG-membrane associated molecule, and second: to get close to cancer cells for phagocytosis and destruction. Otherwise, if previously hCG is not positively polarized, immune cells could not be able to get close to cancer'cells for phagocytosis and destruction. According to investigations already mentioned, ABA is used in human body clearly as a cytokine but, this hormone also stimulates production of other cytokines as tumor necrosis factor alfa (TNFALFA) and prostaglandins $E_2$ ($PGE_2$). Invention of Zocchi et al., 2008, demonstrates that, among other cytokines, TNFALFA is increased by ABA effect specifically in human monocytes, murine microglia and murine macrophages. Biologists have proposed that, a cell commits suicide by apoptosis when it triggers death activators as TNFALFA, TNFBETA and FAS ligand binding to receptors at the cell surface. Also, research of Scarfi S and Zocchi E, and collaborators, on 2008, titled "Cyclic ADP-Ribose-Mediated Expansion and Stimulation of Human mesenchymal stem cells (MSC) by the Plant Hormone Abscisic Acid", mentions that ABA stimulates functional activities of MSC: cyclooxygenase 2-catalized production of $PGE_2$, release of several cytokines known to mediate the trophic and immunomodulatory properties of MSC, and chemokinesis.

Thus, it may be seen herein the enormous importance of the immune system in control and destroy cancer cells. When the immune system is depressed, for example in HIV patients, in these patients arise cancer, such as Kaposi's Sarcoma. In 1909, Ehrlich P, correctly proposed that the incidence of cancer would be much greater without the usefulness of the vigilance of our immune defense system in identifying and eliminating tumor cells.

Cancer cells are generally recognized and destroyed by immune system cells, but sometimes such cells evade the immune system. Actually, it has been discovered that immune cells as granulocytes use ABA for cell destruction. If ABA is the key molecule used by the human body for cancer cell destruction, and, sometimes these cells evade the immune system, the ABA fluctuating levels and beta carotenes (the precursor of ABA) in blood, and the ABA efficient production by the human metabolism could be important factors to explain cancer evasion. In plants, it has been measured ABA fluctuation in relation to stress. In xylem sap, ABA fluctuates in well watered and water-stressed plants (Wilkinson and Davis 1997). Human stress may increase the ABA levels, but may also consumes its potential levels and precursor sources when metabolized provoking cancer evasion. It has been pointed out correlation between stress and cancer and stress and depression of the immune system.

According to Dr. V. Livingston (U.S. Pat. No. 3,958,025, 1976), ABA presence has been demonstrated in human serum and urine by the R. F. Scand, Jr. Clinic Laboratory Investigation on January 1970. On the same paragraph, it says that, the serum of healthy persons can be demonstrated to have a higher inhibiting effect on plants than that of the sick or afflicted; that is, a greater amount of the inhibitory factor exists in the blood of the well person. In invention of Zocchi et al., 2008, page 3, presence of ABA in human plasma was determined by HPLC-coupled mass spectrometry (HPLC-MS). It was found ABA plasma concentrations in the range of 5-10 nM, of both, the cis-trans isomer (the active form in plants), and the trans-trans isomer.

Correlation of the ideas mentioned above could open new lines of investigations about ABA and the human immune system.

Investigations of Bruzzone et al. 2007 and Zocchi et al. 2008, may be considered significant and an additional evidence that immune system is important for destruction of cancer cells. Therefore, any prior medical treatment, which it compromises the patient immune system, such as chemotherapy or radiotherapy could affect a subsequent ABA treatment or any treatment against cancer. Also, cancer patients that have received prior conventional treatments such as chemotherapy or patients with immune system disorders must be refused to participate in an ABA clinical trial, before it could be demonstrated ABA effectivity in the treatment of cancer without the involvement of the immune system in such treatment.

ABA Expression of Retinoic Acid Receptor Beta, PPAR Gamma, Involucrin Protein and Inhibition of Ki67 Cancer Marker For a long time it has been recognized to retinoic acid (RA) as a signalling molecule influencing developmental processes and cell differentiation. Since 1950, many investigations had proven its limited power as differentiation inducer drug. Nevertheless, it was reported by Khuri et al., 2006, during the largest retinoid chemoprevention trial that, retinoid (ISOTRETINOIN) was not effective against head and neck squamous cell carcinoma.

According to Freemantle et al. 2006, in an article appeared in the editorials of the Journal of The National Cancer Institute vol 98, No 7, it has been discovered that, retinoic acid receptor beta (RARBETA) expression is frequently silenced in epithelial carcinogenesis. It has also led to the hypothesis that, RARBETA acts as a tumor suppressor and is partially responsible for the limited clinical activity of classical retinoids.

Herein, it is important to mention that, under a treatment with ABA, RARBETA is expressed and not silenced by cancer cell. The expression of this receptor has been confirmed by Zhao et al. 2007, in the Key Laboratory of Oral Biomedical Engineering of Ministry of Education, in Sichuan University. The research titled "Effect on Induction of Differentiation of TCA8113 Cells Affected by Abscisic Acid in Vitro", confirms the expression of RARBETA, involucrin protein and caspase-3 mRNA.

According to Donato and Noy 2005, presence of RA is not necessary for over expression of the cellular retinoic acid binding protein II (CRABP II), which is the key protein attaching to RARBETA. Also, they mention that the tumor suppression by RA regulates transcription of multiple genes.

Investigations mentioned above prove that, it is ABA and not RA, which induces and conducts efficiently a process of cell differentiation.

According to Freemantle et al. 2006, apparently retinoids activate transcription by binding to the classical nuclear retinoid acid receptors (RARS) Alfa, Beta and Gamma and also to the non-classical nuclear retinoid x receptors (RXRS). RARS can heterodimerize with RXRS, whereas RXRS heterodimerize with other nuclear receptors, including the thyroid hormone receptor, the vitamin D receptor, and the peroxisome proliferator-activated receptors (PPAR).

The invention of Bassaganya-Riera et al. 2007, Number WO2007/092556A2, titled "Method of Using ABA to Treat and Prevent Diseases and Disorders", teaches that PPAR gamma forms a heterodimer with RXR and undergoes a conformational change that allows it to recruit coactivators. The primary outcome of the PPAR-controlled transcriptional regulation of genes is a reduction in the hyperlipidemia, hyperglycemia, and hyperinsulinemia. The invention is based in that, ABA can affect the expression of PPAR Gamma and relates to prevention and/or treatment of hyperglycemia, impaired glucose tolerance, insulin resistance, prediabetes, and Type 2 diabetes, while in other embodiments, the invention relates to prevention and/or treatment of inflammation, including but not limited to obesity-related inflammation.

Also ABA capacity in diabetes treatment is disclosed in an invention of Bruzzone S et al. 2008, from the Department of Experimental Medicine, Section of Biochemistry and Center of Excellence for Biomedical Research, University of Genova. The invention titled "ABA is an Endogenous Stimulator of Insulin Release from Human Pancreatic Islets with Cyclic ADP Ribose as Second Messenger" teaches that, ABA is an endogenous stimulator of insulin secretion in human and murine pancreatic beta cells. They mention that, autocrine release of ABA by glucose-stimulated pancreatic beta cells, and the paracrine production of the hormone by activated granulocytes and monocytes suggests that, ABA may be involved in the physiology of insulin release as well as in its dysregulation under conditions of inflammation.

Moreover, ABA produces additional changes in cancer cell. According to Zhao et al. 2007, the Involucrin protein is expressed during a cancer cell differentiation process of TCA8113 (human oral carcinoma), affected by ABA. In connection to this, other researchers have found that, involucrin protein is expressed when stem cells from basal layers of the human skin are differentiated to form keratinocytes in upper layers. On the other hand, and in agreement to Tang et al. 1996, the nuclear protein Ki67 that is expressed in proliferating tumor cells was reduced by ABA, which decreased such proliferating activity. Ki67 has been used as a cancer marker for cell proliferation of solid tumors and some hematological malignancies.

ABA Involvement in Animal Apoptosis of Senescent Normal Cells

In this invention, it has been suggested ABA role intervention in cell normalization and differentiation processes. Nevertheless, ABA could be implicated in aging and cellular death processes as well. The following several reasons provide evidence that, ABA could hypothetically be involved in apoptosis of senescent normal animal cell: 1. ABA and ethylene have been correlated to the phenomenon of senescence and plant death (see paragraph [0009]). 2. $K^+$ and $Na^+$ decrease effect induced by ABA is exerted without a criterion of selectivity (see paragraph [0147]). It suggests that ABA would cause the decrease of $Na^+$ and small amounts of $K^+$ in cancer cells and would either cause the decrease of $K^+$ and small amounts of $Na^+$ in senescent normal cells. 3. Apoptosis of "normal and cancer cells" has been connected to the phenomenon of $Na^+$ and $K^+$ decrease and cell shrinkage (see paragraph [0149]). 4. Plant stress hormones suppress the proliferation and induce apoptosis in human cancer cells (see paragraph [0144]).

ABA Against Human Stress

ABA is considered a hormone biologically designed by nature to defend plants against stress. ABA enhances plant adaptation to various stresses such as cold tolerance, salt osmotic adjustment and drought (Zeevaart et al., 1988). In addition, ABA-glucose ester (physiologically inactive form of ABA) accumulates in plant tissues with the age and during stress treatments (Dietz et al., 2000). Those considerations could open new insights and investigations concerning ABA.

ABA plant stress adaptation could have been transferred to animals during the evolution, under the form of defense mechanisms against physical, mental and emotional stress. Mechanisms such as ABA cellular apoptosis and aging could be the ending consequences of human stress assimilation. ABA anti-stress mechanisms could take place, because ABA release of acute stress could have an antagonistic action and interactive effect with adrenalin and glucorticoids, both hormones released by the adrenal glands.

During stress, elevated levels of the human stress hormone cortisol counteract insulin by increasing gluconeogenesis. Cortisol also slows the production of good prostaglandins, increases hyperglycemia and blood pressure, and weakens the activity of the immune system. ABA opposite action, helps to release insulin from pancreatic islets (Bruzzone S et al. 2008, see paragraph) [0169]), reduces hyperglycemia (Bassaganya-Riera et al. 2007, see paragraph [0168]), stimulates release of $PGE_2$ by MSC (Scarfi et al. 2008, see paragraph [0156]), and strengths the immune system by stimulating granulocytes and other immune system cells (Bruzzone et al. 2007, Zocchi et al. 2008, see paragraph [0154]). Also, good $PGE_2$ support immune function, dilate blood vessels, inhibit thick blood and are anti-inflammatory.

ABA G-Protein Signalling Pathway

According to Kennedy B—K 2003, from Penn State University, plants respond to environmental stresses with a sequence of molecular signals known in humans and other mammals as the G-protein signalling pathway.

In human cells, this mechanism has been recognized as responsible in regulating either the opening of ion channels and activities of intracellular enzymes. Coursol et al. 2003, p. 651, in the research "Sphingolipid signalling in *Arabidopsis* Guard Cells Involves Heterotrimeric G Proteins", showed that a metabolite denominated, sphingosine-1-phosphate (SIP), functions in animals as an intracellular messenger and an extracellular ligand for G-proteins-coupled receptors of the receptor family, regulating diverse biological processes. In this research it was discovered in *Arabidopsis* that, SIP is a signalling molecule involved in ABA regulation of guard cell turgor. It also was reported that, an enzyme responsible for SIP production, sphingosine kinase (SPHK), is activated by ABA in *Arabidopsis thaliana* and is involved in both, inhibition of stomatal opening and promotion of stomatal closure.

In human cells, ABA G-protein signalling pathway has been confirmed. ABA stimulates several functional activities in human granulocytes (Bruzzone et al. 2007, page 5759) and stimulates insulin release in human pancreatic islets (Bruzzone et al. 2008, page 32188). Both researches point out that, ABA effect is produced through an identical signalling pathway sequentially involving a pertussis toxin (PTX)-sensitive G protein/receptor, protein kinase A activation, ADP-Ribosyl cyclase phosphorylation, and consequent cyclic-ADP ribose over-production, leading to an increase of the intracellular $Ca^{2+}$ concentration (see paragraph [0018]).

Several studies have demonstrated that, ABA effect on drought, cold and high salt, results in $Ca^{2+}$ levels rapid increase in plant cells (Tuteja 2007, page 136). Correlation of studies of Bruzzone et al. 2007, 2008 and Tuteja 2007, reveals that ABA signalling $Ca^{2+}$ increase is a similar and paralleled mechanism, which it occurs in plants as in animals as well.

ABA $Ca^{2+}$ influx and $K^+$ efflux are mechanisms sequentially connected, in ABA transduction. According to Schroeder et al. 2001, in guard cells, ABA induces cytosolic $Ca^{2+}$ elevations, which activates anion release. This causes guard cell depolarization, which activates outward-rectifying K$^+$ channels, resulting in K$^+$ efflux and stomatal closure. K$^+$ efflux finally causes membrane hyperpolarization. A large percent of drugs approved for use in humans target the G-proteins signalling pathway.

Preparation of the Medication. Curve of Uptake Efficiency of ABA

Understanding how ABA works in plants could open new insights for cancer treatments and applications. Stoma pH changes generated by light have been thought to occur in relation to photosynthesis. A CO$_2$ concentration reduction in guard cells as a result of photosynthesis consumption causes a pH rise. During the darkness, photosynthesis stops, and CO$_2$ concentration rises as a result of respiration (Devlin, 1966, p. 72). The latter phenomenon produces a pH decrease according to photosynthesis reaction linked to carbonic acid (H$_2$CO$_3$) equilibrium:

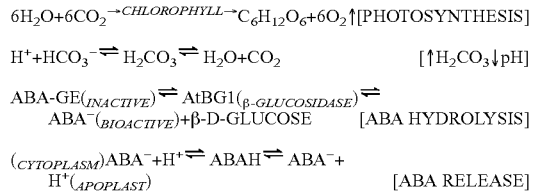

Mesophyll and epidermis cells of leaves also intervene in the stomata response. Such cells are able to store ABA when intracellular pH is relatively high during the day, but at night intracellular pH decreases and ABA is released outside plasma membrane, activating it stomatal closure (see β-glucosidase action in paragraph [0015]). This daily cycle and pH changes can be understood through the ion trapping concept of ABA.

ABA is a weak acid, which preferentially acumulates in the more alkaline compartments of the leaf. At an acidic pH (5.2 to 6.5) more ABA will be present in its lipophilic undissociated form (ABAH). Such form can diffuse across the plasma membrane into the more alkaline compartments of the cytoplasm. In such mesophyll and epidermis cell compartments, which have a pH between 7.2 and 7.4, it dissociates to lipophobic form (ABA$^-$ and H$^+$), which becomes trapped inside the cell (Hartung and Slovik 1991).

ABA physiological behavior, in relation to an extracellular pH in plant cells, will be taken as reference for choosing the right pH for a buffer solution. It will permit to figure out consequentially, a pH of the medication to get the best ABA treatment against human cancer cells. This medicine has not before been applied in humans by intravenous way, therefore ABA plant physiology is the unique available reference.

An ABA efficient response in plants can be evaluated by its capacity to inhibit stomatal opening or stimulating stomatal closure. ABA concentration applied via extracellular, and, medium pH are important factors. Anderson 1994, p. 1177, found that 10 mcM ABA extracellular application, inhibited stomatal opening by 98% at pH 6.15 and by 57% at pH 8.0. In this same research, he also mentioned that, a pH dependence of extracellular ABA action might suggest a contribution of an intracellular ABA receptor in stomatal regulation. In agreement to Allan et al. 1994, p. 1107, ABA on guard cells is more effective at pH 5.5, than at pH 7. Other several researchers, also found that ABA was much more effective in closing stomatal pores at an acidic extracellular pH (Ogunkanmi et al. 1973, Kondo et al. 1980, Kondo and Maruta 1987, Paterson et al. 1988). If the extracellular medium pH ranges between 5.2 and 6.5, ABA produces stomatal closure at first contact and signal, but also at this pH, the molecule rapidly gets across the plasma membrane (Hartung and Slovik 1991, see paragraph [0181]). Thus, the hormone gets in contact with intracellular receptors, by which it starts to open stomata. According to Ilan et al. 1994, an extracellular pH reduction from 8.1 to 5.5 significantly reduced outward K$^+$ currents. Likewise, Blatt 1992, found that acidic extracellular pH activated inward K$^+$ channels in Vicia faba guard cells (cited in Wilkinson and Davis 1997, page 569). Specifically the last two researches describe up a sequential and combined phenomenon, where the plant hormone ABA, produces: first a stomatal closure and solute exit, and, second a stomatal opening and solute reentry. This phenomenon links ABA to a combined phenomenon of stomatal closure and opening in connection to an acidic extracellular pH range. Nevertheless, a question need to be responded: what would be the ABA effect in an alkaline extracellular medium?.

Astle et al. 1980, detected an ABA carrier restricted to root apical tissue that, was dependent on a membrane pH gradient, but not on a membrane electrical gradient. According to Wilkinson and Davis 1997, pp 571-572, this carrier was responsible for a portion of the ABA taken up by epidermal simplest at an extracellular pH 6.0. They mentioned that both, carrier-mediated and the diffusive uptake contribute to the efficiency of ABA sequestration by this tissue at extracellular pH 6.0. Mostly important and in agreement to them, the carrier becomes inactive at an extracellular pH 7.0, when diffusive uptake is reduced and ABA accumulates in the apoplastic compartment in the intact leaf. This investigation discloses that, ABA carrier is inhibited at pH 7.0 and higher. Thus, the plant hormone is not transported toward cell cytoplasm, by which is unable to get in contact with intracellular receptors for producing stomatal opening. If pH of the extracellular medium is held at a pH between 7.2 and 7.4, ABA is not able to diffuse across the plasma membrane because it dissociates to ABA$^-$ lipophobic form (Hartung and Slovik 1991, see paragraph [0181]). It can be observed in the FIG. 8 of the present invention that, ABA uptake is zero at an extracellular pH 6.5 and higher. At pH ranging between 5.2 and 6.5 the molecule tends to produce a combined effect of stomatal closure and opening. This effect produces exit and reentry of cations. In an alkaline medium pH, ranging between 6.5 and 7.4, ABA tends to induce just stomatal closure and exit of cations.

ABA uptake must be measured as function of the following variables: stomatal closure and opening, the extracellular medium pH, plasma membrane inside and outside receptors, and saturable ABA uptake component (carrier). ABA taken up or not will determine, consequent hormone effect in producing cancer cell normalization or apoptosis.

Hornberg et al. 1984, pp. 321-323, found occurrence of a high-affinity guard cell specific ABA-binding proteins facing the apoplasmic space. Most importantly they detected two types of ABA receptor designated sites on plasma membrane.

Microinjections of ABA into guard cells did not inhibit stomatal opening (Anderson 1994, p. 1182, and, Popova 2000, p. 379). Such data mostly provides evidence that, a reception site for ABA is on an extracellular side of the plasma membrane, nevertheless, research of Pedron et al. 1998, p. 390, agrees with a dual location of ABA reception sites (intracellular and out-facing plasma membrane). They express that, presence of intracellular receptors is in agreement to evidence that, cells also respond to intracellular ABA.

An ABA uptake theoretical curve (60), correlates ABA uptake concentrations in percents (62) and pH values of a medium outside the plasma membrane (64). It has been drawn in the FIG. 8, according to the Henderson-Hasselbalch equation:

pH=pK+log [conjugate base]/[conjugate acid]

As the protonated or undissociated form of ABA is ABAH, and the anion is ABA⁻, the mentioned equation results as:

pH=pK+log [ABA⁻]/[ABAH]

In the equation ABA pK has a value of 4.7 (70).

pH values in variable (64) were calculated by considering relative concentrations in percent (62), of two different forms of ABA.

Figure 8:
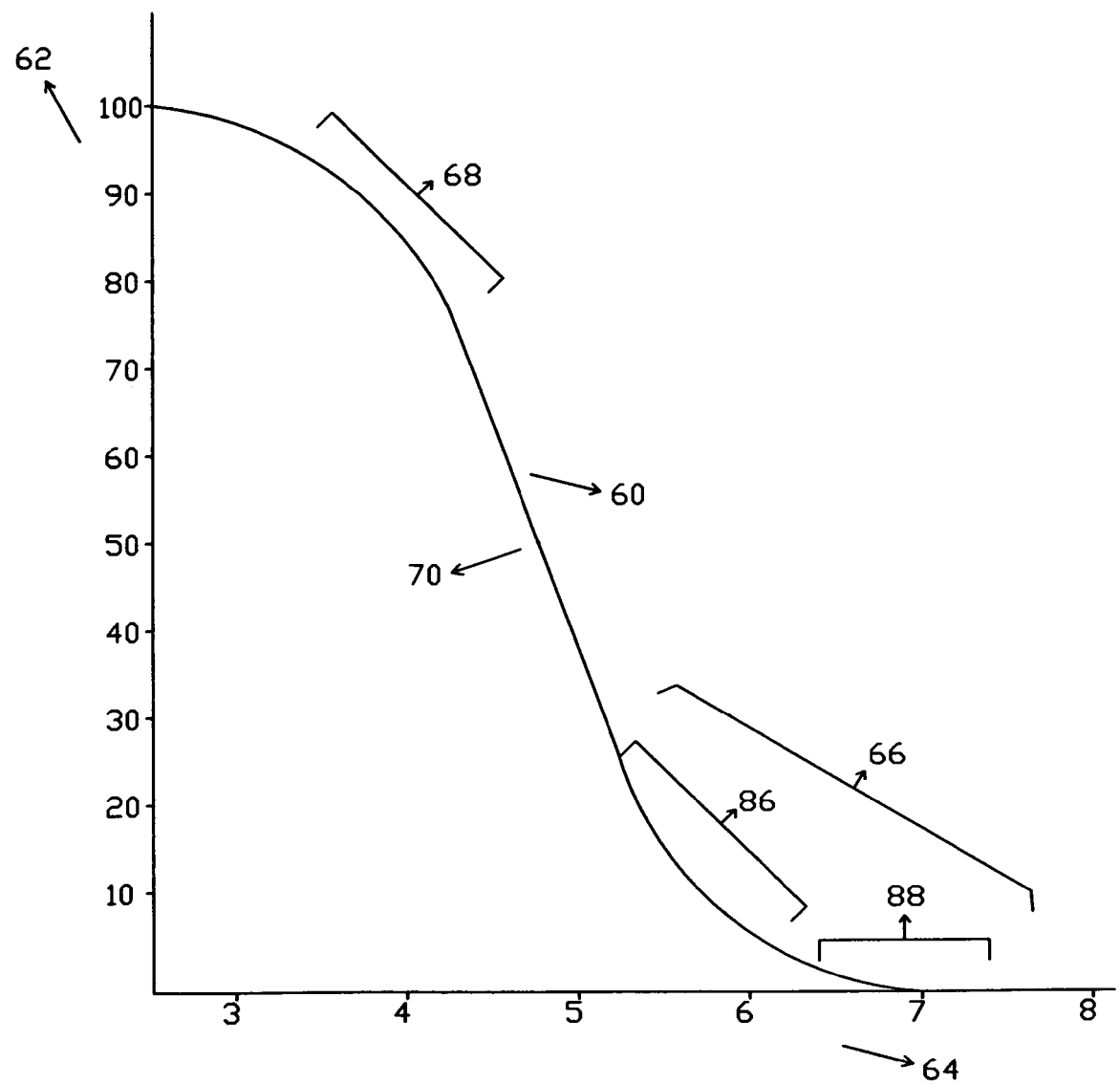
FIG. 8 is an illustration of the curve of ABA uptake.

As it can be observed in the FIG. 8, (ABAH) uptake concentrations (62) increase when it decreases pH values (64), therefore, in acidic medium ABAH can easily get across plasma membrane. According to the FIG. 8, a range of pH between 5.2 and 7.4 varies to produce a differential effect for the maximum efficiency of stomatal closure (66). At pH medium ranging between 5.2 and 6.5, ABA produces a phenomenon of cell normalization or differentiation (86). At pH ranging between 6.5 and 7.4 (88), ABA induces an apoptotic phenomenon. Conventional cancer treatments have been designed to control the disease via destruction of cells. ABA is classified and cataloged as a differentiation inducer drug. This group of agents have the natural property to control and fight cancer via conducting tumor cells to be reversed in normal cells. Cancer cell destruction by apotosis is useful in determined patients, but not in all, such treatment is not in agreement to the perse ABA essential conception as differentiation inducer drug. In general, apoptosis causes cancer cell destruction and toxin unload to the blood patient. ABA buffer medication elected with the intention of inducing apoptosis brings a bigger risk to patients with terminal types of cancer. ABA buffer medications for inducing "cell normalization or apoptosis" must be differentially applied to cancer patients by physician criterion (see aside of the operation).

In addition, it is possible to observe on the curve (60), an area of stomatal opening maximum efficiency (68), which is produced at a pH 5.2 and lower. At this point, ABA absorption has been completed in order to full maintain the phenomenon of stomatal opening.

Concentrations and Medication Dosage

In survey of Hartwell 1982, an enormous quantity of plant species has been found in showing properties against different types of cancer, generating it perceptible benefits. In plants, ABA concentration is considered relatively very low; notwithstanding ABA is the common factor found in all species of plants. ABA concentrations in unstressed leaves range approximately between 800-1500 ng/100 g of fresh weight, meanwhile, in water stressed leaves ABA ranges between 1700-10000 ng/100 g of fresh weight (Singh et al. 1979, p. 136). According to this research, ABA levels increased due to water deficit by at least in an average of 2-7 fold. Other researchers mention that ABA level increased in about 30 and even 200 fold. In xilem sap of well watered sunflower plants, ABA concentration ranges between 1.0 and 15.0 nmol/dm³, and in water-stressed of the same specie ABA can reach 3.0 mcmol/dm³ (Wilkinson and Davis 1997).

ABA concentrations in animals as pigs ranged between 13-180 ng/100 g of fresh weight tissue in different organs. In rats fed with diet containing ABA, concentration was determined between 248-429 ng/100 g of fresh weight of brain tissue (Le Page-Degivry 1986, p. 1156). ABA concentration in animals is lower than it is found in plants.

ABA concentrations used in Dr Livingston's experiments in vivo are higher than ABA concentrations usually found in plants, as seen paragraphing [0194]. The most efficient group, showed in the experiment, was the number II, with 90% of survivors and a lower dose (1 mg/kg). Such concentration can be taken as a reference and defined as equivalent to 1 mg/ml.

Nevertheless, doses can range between 0.1 mg/kg and 20 mg/kg, and concentrations between 0.1 mg/ml and 50 mg/ml. Doses may vary according to an application system.

ABA effect must be reproduced once again by repetitive doses, because ABA is metabolized and it induces a transient effect. ABA is involved in homeostatic mechanisms in plants, by which repetitive doses can produce a more prolonged effect.

Preparation of a Buffer Solution

An ABA medication can be buffered at pH ranging between 5.2 and 6.5 for inducing cell normalization (86), and also can be buffered at pH ranging between 6.5 and 7.4 for inducing cellular apoptosis (88). An optimum pH 6.1 is elected to accomplish cell normalization and an optimum pH 7.0 is elected to accomplish cellular apoptosis. A pH for the buffer medication becomes equal to the pH of the bulk, because the buffer solution containing ABA will hold a pH of the extracellular medium until ABA is absorbed or as long as buffer capacity is permissible. Cancer progression decreases the normal blood pH (84), thus, application of an ABA buffer medication for inducing cell normalization would have a synergetic action in an acidic blood pH. ABA buffer medication for inducing apoptosis would be mostly recommended in patients with normal pH.

A buffer solution for the medication is initially prepared by using the method of Cassiday 1999, pp. 10-11. For the medication, it has been elected the pair carbonic acid and its salt ($H_2CO_3$—$HCO_3^-$), which has a pK=6.1 (78). Graphic of the curve (80) has been showed in FIG. 9 as previous art. Curve is elaborated by the author by applying the Henderson-Hasselbalch equation and plotting values of pH between 4 and 7 (72), and, relative concentrations of carbonic acid (74) and bicarbonate (76) in percents. By far the most important buffer for maintaining acid-base balance in the blood is the carbonic acid-bicarbonate buffer. A simultaneous double equilibrium reaction is given:

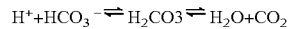

Buffer solution at pH 6.1 is fabricated by using 50% of carbonic acid and 50% of its salt. As pH=pK, buffer solution will have an optimal capacity inside of the region of maximum buffering capacity (82). Buffer solution at pH 7.0 is fabricated by using 12.5% of carbonic acid and 87.5% of its salt.

For the fabrication of an ABA buffer solution, it is important to get in count, the ABA dissociation and pH of the medication. Several researchers have mentioned that ABA is a weak acid that at neutral pH it occurs in a dissociated state; but at acidic pH, it occurs in the protonated form. ABA is highly dependent of the pH and apparently it dissociates as a strong acid. In an aqueous acid-base solution an ABA equilibrium would be maintained by the carboxyl group and the carboxylate anion as follows:

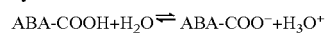

Due to that the carboxylate anion contained in ABA is more stable than the ABA carboxyl group the equilibrium favors the right side of the equation. Water as substituent near the carboxyl group acts to increase the acidity. It makes to ABA a stronger acid with bigger power of dissociation.

Research of Kelen et al. 2004, denominated "Separation of Abscisic acid, Indole-3-acetic, Gibberellic Acid in 99r (*Vitis berlandieri*×*Vitis rupestris*) and Rose Oil (*Rosa damascena* mill.) by Reversed Phase Liquid Chromatography" may help to determine and verify ABA dissociation according the pH. In this study it is considered that, retention in the mobile phase of carboxylic groups which are contained in these hormones depends on the percentage of ionized and non-ionized species. Results proved that, ABA is present in non-ionized form at approximately pH 4.0. Measurement of ABA pK value in the assay was calculated (pK=5.82) at 30% of acetonitrile. The ABA dissociation in the assay can be verified by using the Henderson-Hasselbalch equation as follows:

$$pH = pk + \log[BASE/ACID] \to 4 = 5.82 + \log[BASE/ACID]$$

$$-1.82 = \log[BASE/ACID] \to \text{antilog}(-1.82) = [BASE/ACID]$$

The result of the calculation is a proportion as follows:

$$[BASE/ACID] = 0.015 = 0.15/100[0.15\%(BASE) - 99.9\%(ACID)*]$$

Also retention factors can be transformed in percents of non-ionized and ionized forms and tabulated as follows:

| RETENTION FACTOR | pH | % OF NON-IONIZED (ABAH) | % OF IONIZED (ABA$^-$ + H$^+$) |
|---|---|---|---|
| 3.53 | 4 | 99.9* | 0.1 |
| 3.52 | 4.5 | 99.6 | 0.4 |
| 3.41 | 5 | 96.5 (100) | 3.5 (0) |
| 2.55 | 5.5 | 72.1 (70) | 27.8 (30) |
| 1.54 | 6.0 | 43.5 (40) | 56.4 (60) |
| 0.48 | 7.0 | 13.5 (10) | 86.4 (90) |

Above results were rounded to obtain a better view and correlation made below with research of Honberg et al. 1984.

Hornberg et al. 1984, pp. 321-323, found occurrence of a high-affinity guard cell specific ABA-binding proteins facing the apoplasmic space. They detected three different designated sites: as anion (one site) and for ABA in its protonated form (two sites). Such proportion means that, 30% of the receptor sites facing outside attach to ABA in its anionic form and 60% attach to ABA in its protonated form. Herein, it is strongly believed that a proportion of ABA receptor designated sites inside of cell is inverse or opposite to the Honberg structure of receptor designated sites facing the apoplasmic space.

Theoretically, it may be considered the receptor anionic site as an "ABA activator receptor site" which induces stomatal closure and stomatal opening. Likewise, the receptor protonated site may be considered as an "ABA carrier receptor site" which induces ABA absorption and transportation to the cell inside.

At pH 7, 90% of ABA dissociates, but only 30% is attached to the plasma membrane anionic site. It keeps an ABA plant economy in relation to the sequestration of the molecule. Most importantly, this mechanism stimulates: plant stomatal closure when ABA attaches to outside anionic receptors, and, stomatal opening when it attaches to same receptors into the cell inside. In transformed retention factors of Kelen et al. 2004, it can also be observed that, at pH 6, ABA attaches to both types of receptors inducing stomatal closure and stimulating the molecule to be absorbed. Once, ABA protonated form gets across the plasma membrane, it becomes in its anionic form according to the ABA ion trapping concept. Thus, ABA$^-$ will attach to anionic receptor sites inside of cell producing, a partial or a total phenomenon of stomatal opening.

30% of receptor designated sites must be attached to ABA to produce the partial phenomenon and 60% to produce the total phenomenon.

For making ABA buffer solutions, it will be used an ABA dissociation percentage of 90% at pH 7, and, 60% at pH 6.1. For buffer solutions the ABA concentrations will range between 1 mg/ml and 3 mg/ml to produce a medication with a general concentration not higher than 0.9% W/V (9 mg/ml). The active principle (ABA) is soluble in methanol and is diluted at 50 mg/ml. Additional quantity of methanol, ethanol or another alcohol may be added to the medication to fulfill the pharmaceutical requirements. Molecular weights of the components are: ABA (264.3 gr), NaHCO$_3$ (84.01 gr), H$_2$CO$_3$ (62 gr). By adding ABA to the buffer solutions it will increase the acidity, which must be neutralized by the salt (sodium bicarbonate) according to the following reaction:

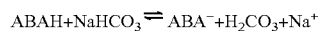

$$ABAH + NaHCO_3 \rightleftharpoons ABA^- + H_2CO_3 + Na^+$$

Because the reaction is equimolar, 1 mol of ABAH will react with 1 mol of NaHCO$_3$. In addition, the medication must include 10% of Polyoxyethylene Sorbitan Monooleate (CAS # 9005-65-6) named also as TW80 and usually used as an emulsifier, solubilizer, surfactant, stabilizer and dispersant. The medication may be fabricated in different volumes: 5 ml injections, and 25 ml infuses, buffered at pH 6.1 and 7 (6.62) as follows:

| MEDICATION | ABA(mg/ml) | VOLUME(ml) | pH |
|---|---|---|---|
| 1 | 3 | 5 | 6.1 |
| 2 | 3 | 25 | 6.1 |
| 3 | 1 | 5 | 7.0 (6.62) |
| 4 | 1 | 25 | 7.0 (6.62) |

Medication Buffered at pH 6.1:

MEDICATION No 1: 3 mg/ml-5 ml H$_2$O–15 mg ABA/0.2 ml H$_2$O+0.3 ml methanol (113.5 mM–dissociated at [60%] 68.1 mM)–15 mg sodium bicarbonate/4.5 ml H$_2$O (39.6 mM)+15 mg carbonic acid/4.5 ml H$_2$O (53.7 mM). After adding ABA the medication molarity is 28.3 mM (base) and 55 mM (acid) calculated it for 5 ml. The pH of the initial medication is verified and calculated through the Henderson-Hasselbalch equation as follows:

$$pH = pka + \log[BASE/ACID] = 6.1 + \log[28.3 \text{ mM}/55 \text{ mM}] = 5.81.$$

As the resultant pH is under the expected value (6.1), the pH of the medication is readjusted at pH 6.1. New concentrations of the base and acid are as follows: 20 mg sodium bicarbonate (52.9 mM)+10 mg carbonic acid (35.8 mM). Final molarity is 40.8 mM (Base) And 39.0 mM (acid). The pH is recalculated:

$$pH = 6.1 + \log[40.8 \text{ mM}/39.0 \text{ mM}] = 6.1$$

MEDICATION No 2: 3 mg/ml-25 ml H$_2$O–75 mg ABA/1 ml H$_2$O+1.5 ml methanol–99.0 mg sodium bicarbonate/25 ml H$_2$O+51 mg carbonic acid/25 ml H$_2$O. Same concentrations, final molarity and pH as in medication No 1.

Medication Buffered at pH 7 (6.62):

MEDICATION No 3: 1 mg/ml-5 ml H$_2$O–5 mg ABA/0.4 ml H$_2$O+0.1 ml methanol (37.8 mM–dissociated at [90%] 34.0 mM)–35 mg sodium bicarbonate/4.5 ml H$_2$O (92.5 mM)+5 mg carbonic acid/4.5 ml H$_2$O (17.9 mM). After adding ABA the medication molarity is 76.4 mM (base) and 22.8 mM (acid) calculated for 5 ml. The pH of the medication is verified as follows:

$$pH = pka + \log[base/acid] = 6.1 + \log[76.4 \text{ mM}/22.8 \text{ mM}] = 6.62$$

Figure 9:
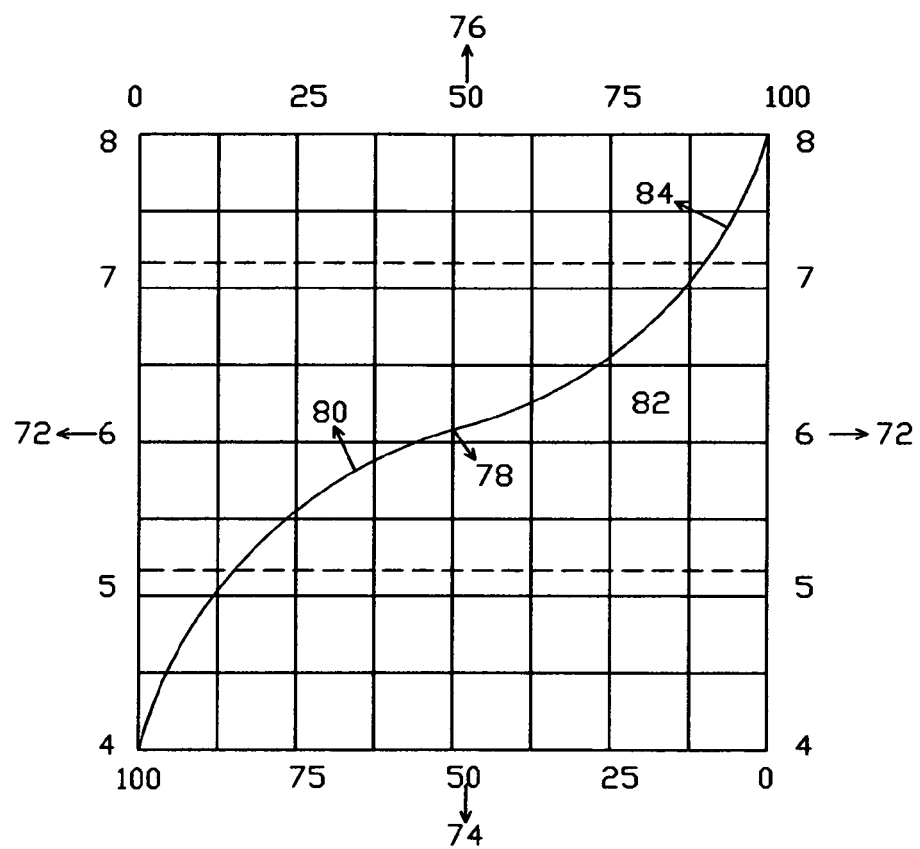
FIG. 9 is a prior art illustration of the curve of a buffer solution.

This resultant pH is not recalculated because, by increasing the percent of the base and decreasing the percent of the acid, the pH of the medication would be out of the region of maximum buffering capacity (see FIG. 9). Thus, it decreases the efficiency of the medication, however, the obtained medication pH is close to the expected value (7.0) and it is found inside of the range for inducing cellular apoptosis (6.5-7.4).

MEDICATION No 4: 1 mg/ml-25 ml H$_2$O–25 mg ABA/ 2.0 ml H$_2$O+0.5 ml methanol–175 mg sodium bicarbonate/25 ml H$_2$O+25 mg carbonic acid/25 ml H$_2$O. Same concentrations, final molarity and pH as in Medication No 6.

Embodiment Number One

A pharmaceutical medicine for an intravenous, intramuscular and subcutaneous treatment may be elaborated by using the buffer system as mentioned before. ABA concentrations can range between 0.1 mg/ml and 5 mg/ml and best range would be between 1 mg/ml and 3 mg/ml. Medication will be prepared by obtaining an isotonic solution not higher than 9 mg/ml (0.9% W/V). Doses range between 0.1 mg/kg and 5 mg/kg. Liquid volume of the medications may vary between 5 ml (injections) and 25 ml (infuses). ABA in plants is conducted from roots to leaves via across the xylem, by which the ABA best application for a cancer treatment would be by intravenous way. ABA application via the human circulatory system would mimic ABA hormonal flow in plant streams and xylems.

ABA Pharmaceutical Liquid Compositions of Embodiment Number One

Pharmaceutical liquid compositions of the medication No 1 and No 2 are as follows:

Medication No 1
ABA concentration=3 mg/ml.
Volume=5 ml
ABA=15 mg (33.3% W/W)–113.5 mM. Dissociation 60% (68.1 mM)
Sodium Bicarbonate=20 mg (44.4% W/W)–40.8 mM.
Carbonic Acid=10 mg (22.2% W/W)–39.0 mM.
Methanol=0.3 ml (6% V/V)
Distilled Water=4.2 ml (84% V/V)
TW80=0.5 ml (10% V/V)
pH=6.1

Medication No 2
ABA Concentration=3 mg/ml.
Volume=25 ml
ABA=75 mg (33.3% W/W)–113.5 mM. dissociation 60% (68.1 mM)
Sodium Bicarbonate=99.0 mg (44.4% W/W)–40.8 mM.
Carbonic Acid=51 mg (22.2% W/W)–39.0 mM.
Methanol=1.5 ml (6% V/V)
Distilled Water=21 ml (84% V/V)
TW80=2.5 ml (10% V/V)
pH=6.1

Pharmaceutical liquid compositions of the Medication No 3 and No 4 are as follows:

Medication No 3
ABA Concentration=1 mg/ml.
Volume=5 ml
ABA=5 mg (11.1% W/W)–37.8 mM. dissociation 90% (34.0 mM)
Bicarbonate=35 mg (77.7% W/W)–76.4 mM.
Carbonic Acid=5 mg (11.1% W/W)–22.8 mM.
Methanol=0.1 ml (2% V/V)
Distilled Water=4.4 ml (88% V/V)
TW80=0.5 ml (10% V/V
pH=6.62

Medication No 4
ABA Concentration=1 mg/ml.
Volume=25 ml
ABA=25 mg (11.1% W/W)–37.8 mM. dissociation 90% (34.0 mM)
Bicarbonate=174.8 mg (77.7% W/W)–76.4 mM.
Carbonic Acid=24.9 mg (11.1% W/W)–22.8 mM.
Methanol=0.5 ml (2% V/V)
Distilled Water=22 ml (88% V/V)
TW8 0=2.5 ml (10% V/V)
pH=6.62

ABA Decay Length in Xylem

ABA in plants is conducted from roots to leaves via across the xylem, by which the ABA best application for a cancer treatment would be by intravenous way. ABA application via the human circulatory system would mimic ABA hormonal flow in plant streams and xylems. ABA decay length in xylem (Lxylem) has been studied by Kramer 2006. Specifically in xylem SAP this factor will depend of the ABA traveling speed in xylem (V), radius of the xylem vessel (R), membrane permeability of ABAH ($P_{AH}$), and ABA effective permeability of sink cells (Peff). Kramer equations are defined as follows:

$$(\text{Lxylem}) = 1.15 RV/\text{Peff} \text{ WHERE Peff} = P_{AH}(1/1+10^{pH-pKa})$$

According to Kramer 2006, page 1235, in the absence of carriers, most of the weak acids have a Lxylem of approximately 2 m or greater. Also in this research, it is pointed out that ABA Lxylem is on the order of the 10 m with variations between 2.2 m at 1 m/h speed and 22 m at 10 m/h speed. Lxylem is proportional to the speed of flow in the xylem. That means that, ABA losses in xylem are proportionately higher at low transpiration rates. If it is introduced a catheter in the arm until it reaches the heart, the pass over distance is about 50 cms. The ABA protonated form in xylem can reach a distance in average 20 times higher than that distance before it becomes absorbed, trapped and metabolized. Kramer equations do not take in count a traverse distance in xylem of the ABA dissociated form. ABA can be considered a hormone that has a long range signalling which is compatible with its function and role against cancer and stress.

Embodiment Number Two

Le Page-Degivry et al. 1986, demonstrated in the article "Presence of Abscisic Acid, A Phytohormone in the Mammalian Brain", that ABA as molecule keeps its structure and properties after it is consumed. In such experiment, rats were fed with an ABA containing diet. Tissue ABA determination by radioimmunoassay, after experiment, detected hormone concentrations between 248 to 429 ng/100 g of fresh weight tissue.

Dr. Livingston's experiment using mice also proved that, a use of ABA by oral via had effectivity killing myeloid leukemia. Nevertheless, better results during the Dr. Livingston's experiment were obtained with a dose at 100 mg/kg (90% of survival) than a dose at 10 mg/kg (60% of survival).

Concentrations used to manufacture capsules can range between 1 mg/gr and 100 mg/gr and 10 mg/kg and 100 mg/kg bodyweight.

ABA active principle can be prepared by using an acceptable carrier as a vehicle, and packing such principle in capsules with a biodegradable dark coating to avoid isomeric changes due to the light.

ABA Pharmaceutical Solid Compositions of Embodiment Number Two

An ABA medical composition also includes a solid composition fabricated in capsules of 250 mg (total weight) at 40 mg/gr ABA concentration, for inducing cell normalization and apoptosis. In it has been included a pharmaceutical carrier as vegetable cellulose which serves as thickening and vehicle agent:

For Inducing Cell Normalization:
ABA 10 mg at (4% W/W)
Sodium Bicarbonate 50.0 mg at (20% W/W)
Carbonic Acid 50.0 mg at (20% W/W)
Pharmaceutical Carrier 140 mg at (56% W/W)

For Inducing Cellular Apoptosis:
ABA 10 mg at (4% W/W)
Sodium Bicarbonate 87.5 mg at (35% W/W)
Carbonic Acid 12.5 mg at (5% W/W)
Pharmaceutical Carrier 140 mg at (56% W/W)
Embodiment Number Three ABA by catheter induction to a determined, or inoperable tumor location, for inducing senescence, can be considered a viable method to control terminal types of cancer. Nevertheless, it may result a more expensive treatment. In causing senescence against cancer, the treatment brings itself an use of an ABA massive dose. Hormone concentration in the medication may be diluted in methanol or ethanol at 50 mg/ml, and administered without buffer by using a catheter. It will permit a fluid passage of the hormone to be directly applied to a tumor.

A (+/−)-Abscisic acid manufactured by Sigma-Aldrich is able to carry the mentioned concentration in ethanol which may be clear to slightly hazy. Such synthetic form of ABA (CAS Number 14375-45-2) is obtained through a plant cell culture tested with 99% of purity. A liquid combination for catheter induction may be elaborated at concentrations between 10 mg/ml and 50 mg/ml including the following components and ranges:
Between 10 mg and 50 mg of ABA
Between 0.1 ml and 1.5 ml of methanol
Between 5 ml and 20 ml of distilled water ABA Production, Marketing Forms and Handling Production of ABA by using the fungus *Cercospora rosicola* as mentioned by Assante et al. 1977, pp. 1556-1557, can carry out a commercial level. A strain denominated, *Cercospora rosicola* Passerini, frequently found on *Rosa* sp, produces 6 mg/100 ml maximum of ABA. It must be cultivated on a potato-agar medium, at pH 6.5-6.8, under 24 degrees Centigrade in the light for 30-40 days.

ABA production obtained from *C. rosicola* is considered high, whether it is compared with ABA yields from plant materials. Addicott et al. 1969, p. 142, showed that such yields of plants ranged between 7 and 40 mcg/kg. A higher yield of 9 mg was obtained by processing 225 kg of dry weight from *Gossypium* fruit, which yielded 40 mcg/kg.

Other strains of ABA fungi sources include *Cercospora cruenta, Botrytis cinerea, Ceratocystes coerulescens, C. fimbriata, Fusarium oxysporum,* and *Rhizoctonia solani* (Zeevart et al., 1988). An invention of the Chengdu Institute of Biology Academy of Sciences named, "A New Process for Preparing Natural Abscisic Acid" 2008, uses a fungus to isolate ABA, through a method of fermentation.

From Sigma-Aldrich, different forms of ABA (CAS Number 21293-29-8, molecular weight 264.32) can be purchased, such as: (+) Abscisic acid 99% purity as the natural occurring; (+/−) CIS, trans-Abscisic acid-3H (G) 95% purity as synthetic substance; (+/−) Abscisic acid 98-99% purity as synthetic substance; (+) Abscisic acid 98% purity as natural isomer; (−) CIS, trans-Abscisic acid as racemic or enantiomer. ABA price listed for controlled laboratory use oscillates around $60/100 mg. The cost of each ABA buffered medication is as follows:

| MEDICATION | ABA(mg/ml) | VOLUME(ml) | ABA(mg) | COST($) |
|---|---|---|---|---|
| 1 | 3 | 5 | 15 | 9 |
| 2 | 3 | 25 | 75 | 45 |
| 3 | 1 | 5 | 5 | 3 |
| 4 | 1 | 25 | 25 | 15 |
| CAPSULES | 40 mg/gr | 250 mg (W) | 10 | 6 |

Pharmaceutical material must be handled under protection from light and at specified and variant storage temperatures.

Side Effects

Dr. Livingston reported during experimental observation, that ABA apparently had no toxic side effects in mice even when administered (i.p) in amounts up to 10% by weight of mice. Thus, considering 28 g body weight mouse and ABA (i.p) administered at 2800 mg per week, ABA had no adverse side effects. Nevertheless, ABA definitively can not be prescribed during pregnancy due to existence of hCG in placenta. ABA, being able of neutralizing hCG might cause abortion and also may inhibit and interfere in mammal reproduction. An efficacious medicine against hCG and cancer must have a similar effect against human reproduction, due to the reported presence of hCG in placenta, human fetus, embryos and human spermatozoa. According to Acevedo 2002, malignant transformation and human reproduction share common genetic (evolutionary) and biochemical pathways related to hCG. Moreover, ABA has been found and related to inhibition of insect reproduction in low dosage amounts and having a direct ovicidal effect (U.S. Pat. No. 4,434,180 of Visscher S, N 1984). Also in agreement to Verhaert P and DeLoof A 1986, a peptide similar to the vertebrate gonadotropin has been described in the central nervous system of the cockroach (*Periplaneta americana*). Correlation of former statements produces the strong indication that, ABA could interfere in human reproduction under a natural, non-lethal, sensitive and variant way in direct relation to the ABA fluctuating levels in human blood. An adequate ABA level in blood would be, not too high to produce anticonceptional effect and temporary infertility, but not too low to control cancer cells and human stress.

Operation

Radiation or chemotherapy administered before, during or after ABA treatment is not recommended, because those traditional treatments weaken the patient's immune system. A simultaneous and coordinated action adopted from a patient and physician, strengthening the immune system and neutralizing hormone of cancer will be an indicated treatment against cancer, under the specifications of this invention. Also, a patient diet with high consumption of caratenoids (the ABA precursor) is highly recommended.

Destruction of cancer tissues by any treatment also it brings to a process of released toxins, which might poison other tissues conducting to coma and death. Therefore, it is recommended in a patient recovery process any method for detoxifying the human organism during ABA treatment. Also it is advisable to start an ABa treatment, after large tumors have been removed by surgical procedures. Physicians can elect two different ABA buffer medications, which they may produce distinct effect and differential toxin unload to the blood patient. It is recommended an use of an ABA buffer medication for inducing cell normalization to: patients with a critical health condition; in terminal types of cancer; patient with inoperable large tumors; for elderly patients and for those in which toxins can compromise the patient life or vital organs; and for patients with damaged organs of excretion as colon, kidneys and liver. Likewise, it is recommended ABA buffer medication for inducing apoptosis to: cancer patient with moderate or relatively good condition; in early stage of cancer; young patients; and in those with small tumors where toxin unload released from cancer cell destruction or apoptosis does not compromise the life of a cancer patient.

During the fabrication of the medication, the election of the ABA active ingredients is important. it has been pointed out, differences in ABA catabolism and uptake, between natural ABA and racemic compounds. According to Mertens R et al. 1982, in leaf discs of *V. Faba*, natural ABA (S) was catabolized much more rapidly than the racemic ABA (R), the half-lives were 6-8 hours and 30-32 hours, respectively (cited in Zeevaart JAN A. D et al. 1988).

Conclusions

Clearness about existing compatibility, between ABA as medicine to fight cancer and the disease, is evident and can be perceived through the invention. Any medicine proposed for cancer must come into the conjunction of the recovery process mechanism of Dr. Gerson. Apparently, the electron transfer in cancer cell membrane is just a consequence of a chain of reactions caused by ABA. Electron transfer is a complex and transient event in the middle of diverse and multiple reactions.

Ideas, theories and references of the invention can be used as tools for better understanding the nature, so as expressed in general terms by Ho in 1993: "As in any attempt to understand, we use whatever tools we have at our disposal to help us think, and good scientific theories are just that a superior kind of tools for thought".

It will be apparent to those skilled in the art that, modifications can be made without departing from the object and scope of the present invention. Therefore, it is intended that the invention only be limited by the claims.

What is claimed is:

1. A medical composition for treating mammals in a determined amount and pH sufficient to stimulate the level or activity of an abscicic acid-G-protein pathway and ion channel upon a damaged cell, comprising in combination:
   between 5.0 and 75.0 mg abscisic acid,
   between 20.0 and 174.8 mg sodium bicarbonate,
   between 5.0 and 51.0 mg carbonic acid,
   between 0.10 and 1.5 ml methanol,
   between 4.2 and 22.0 ml distilled water,
   between 0.50 and 2.50 ml TW 80,
   whereby the combination has a pH of between 6.1 and 6.62, and
   whereby the pH composition at 6.1, increases the absorption of abscisic acid in said damaged cell and produces a cell normalization, and
   whereby the pH composition at 6.62, decreases the absorption of abscisic acid in said damaged cell and produces a cellular apoptosis.

2. The medical composition as set forth in claim 1 for cell normalization and pH 6.1, wherein the medical composition includes a liquid volume of 5 ml with:
   15 mg abscisic acid at a 3 mg / ml concentration (33.3% W/W) and 113.5 mM,
   20.0 mg sodium bicarbonate (44.4% W/W) and 40.8 mM,
   10.0 mg carbonic acid (22.2% W/W) and 39 mM,
   0.30 ml methanol (6% V/V),
   4.2 ml distilled water (84% V/V), and
   0.50 ml TW 80 (10% V/V).

3. The medical composition as set forth in claim 1 for cell normalization and pH 6.1, wherein the medical composition includes a liquid volume of 25 ml with:
   75 mg abscisic acid at a 3 mg / ml concentration (33.3% W/W) and 113.5 mM,
   99 mg sodium bicarbonate (44.4% W/W) and 40.8 mM,
   51 mg carbonic acid (22.2% W/W) and 39 mM,
   1.5 ml methanol (6% V/V),
   21.0 ml distilled water (84% V/V), and
   2.50 ml TW 80 (10% V/V).

4. The medical composition as set forth in claim 1 for cellular apoptosis and pH 6.62, wherein the medical composition includes a liquid volume of 5 ml with:
   5 mg abscisic acid at a 1 mg / ml concentration (11.1% W/W) )and 37.8 mM,
   35.0 mg sodium bicarbonate (77.7% W/W) and 76.4 mM,
   5.0 mg carbonic acid (11.1% W/W) and 22.8 mM,
   0.10 ml methanol (2% V/V),
   4.4 ml distilled water (88% V/V), and
   0.50 ml TW 80 (10% V/V).

5. The medical composition as set forth in claim 1 for cellular apoptosis and pH 6.62, wherein the medical composition includes a liquid volume of 25 ml with:
   25 mg abscisic acid at a 1 mg/ml concentration (11.1% W/W) and 37.8 mM,
   174.8 mg sodium bicarbonate (77.7% W/W) and 76.4 mM,
   24.9 mg carbonic acid (11.1% W/W) and 22.8 mM,
   0.50 ml methanol (2% V/V),
   22 ml distilled water (88% V/V), and
   2.50 ml TW 80 (10% V/V).

6. The medical composition of claim 1 wherein a total concentration of the medical composition is not higher than 0.9% W/V (9 mg/ml), and is prepared as an isotonic solution to equal human blood concentration.

7. The medical composition of claim 1 wherein said damage cells are found and detected in diseases and disorders, comprising all types of cancer and malignant tissue, chemical and mechanical damage, aging and in diseases related with the expression of a human and microbic chorionic gonadotropin hormone (hCG).

8. The medical composition of claim 1 wherein an administration of the medical composition is applied to a patient with cancer.

9. The medical composition of claim 1 wherein an administration of the medical composition is applied to a patient with cancer.

10. The medical composition of claim 1 wherein the medical composition is applied by repetitive doses every two days at treatment volumes varying in between a 5 ml injection and a 25 ml infuse.

11. The medical composition of claim 1 wherein the medical composition is applied by subcutaneous administration.

12. The medical composition of claim 1, comprising for oral via abscisic acid concentrations ranging between 1 mg/gr and 100 mg/gr, and doses ranging between 10 mg/kg and 100 mg/kg body weight.

* * * * *